US011529183B2

United States Patent
Smith

(10) Patent No.: US 11,529,183 B2
(45) Date of Patent: *Dec. 20, 2022

(54) POWER AND BI DIRECTIONAL DATA INTERFACE ASSEMBLY AND SURGICAL SYSTEM INCLUDING THE SAME

(71) Applicant: Covidien LP, Mansfield, MA (US)

(72) Inventor: Robert B. Smith, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 16/883,142

(22) Filed: May 26, 2020

(65) Prior Publication Data
US 2020/0281641 A1    Sep. 10, 2020

Related U.S. Application Data

(63) Continuation of application No. 14/966,832, filed on Dec. 11, 2015, now Pat. No. 10,695,119, which is a (Continued)

(51) Int. Cl.
*A61B 18/12* (2006.01)
*H02J 50/10* (2016.01)
(Continued)

(52) U.S. Cl.
CPC ........ *A61B 18/1233* (2013.01); *H02J 7/0013* (2013.01); *H02J 7/0042* (2013.01);
(Continued)

(58) Field of Classification Search
CPC .... A61B 18/1233; H02J 50/10; H02J 7/0013; H02J 7/0027
(Continued)

(56) References Cited

U.S. PATENT DOCUMENTS 3,690,313 A    9/1972  Weppner et al.
4,550,727 A   11/1985  Rexroth
(Continued)

FOREIGN PATENT DOCUMENTS

EP    1943958 A1    7/2008
EP    2218409 A1    8/2010
(Continued)

OTHER PUBLICATIONS

European Search Report for application No. 16 20 3121 dated May 22, 2017.
(Continued)

*Primary Examiner* — Richard V Muralidar

(57) ABSTRACT

A surgical system includes a power supply, a surgical instrument, and a power and data interface assembly. The power and data interface assembly includes a transformer having a primary winding and a secondary winding, a first modulator coupled to the primary winding and configured to receive a power signal from the power supply, a first demodulator coupled to the secondary winding, a second modulator coupled to the secondary winding, a second demodulator coupled to the primary winding, and at least one capacitor configured to tune the primary winding to a first resonant frequency and tune the secondary winding to a second resonant frequency different than the first resonant frequency.

20 Claims, 13 Drawing Sheets

Related U.S. Application Data continuation-in-part of application No. 14/259,819, filed on Apr. 23, 2014, now Pat. No. 9,872,723.

(60) Provisional application No. 61/881,536, filed on Sep. 24, 2013.

(51) Int. Cl.
| | | |
|---|---|---|
| *H02J 7/00* | (2006.01) | |
| *A61B 17/32* | (2006.01) | |
| *A61B 18/14* | (2006.01) | |
| *A61B 17/295* | (2006.01) | |

(52) U.S. Cl.
CPC ........ *H02J 7/0063* (2013.01); *H02J 7/00712* (2020.01); *H02J 50/10* (2016.02); *A61B 17/295* (2013.01); *A61B 18/1445* (2013.01); *A61B 2017/320093* (2017.08); *A61B 2017/320094* (2017.08); *A61B 2017/320095* (2017.08); *A61B 2018/1226* (2013.01); *H02J 2310/22* (2020.01)

(58) Field of Classification Search
USPC ........................................................ 320/108
See application file for complete search history.

(56) References Cited

U.S. PATENT DOCUMENTS

| | | | |
|---|---|---|---|
| 5,807,253 | A | 9/1998 | Dumoulin et al. |
| 5,913,817 | A | 6/1999 | Lee |
| 6,326,884 | B1 | 12/2001 | Wohlrabe |
| 6,547,786 | B1 | 4/2003 | Goble |
| 6,650,229 | B1 | 11/2003 | Wuidart et al. |
| 8,443,476 | B2 | 5/2013 | Hilscher et al. |
| 8,451,032 | B2 | 5/2013 | Dong et al. |
| 8,600,334 | B2 | 12/2013 | Feldchtein |
| 8,932,291 | B2 * | 1/2015 | Orszulak ............ A61B 18/1445 606/42 |
| 9,287,735 | B2 | 3/2016 | Ryu |
| 9,667,084 | B2 * | 5/2017 | Pigott ..................... H02J 50/90 |
| 9,872,723 | B2 * | 1/2018 | Smith ..................... H02J 50/10 |
| 10,695,119 | B2 * | 6/2020 | Smith .................... H02J 7/0063 |
| 2007/0126372 | A1 | 6/2007 | Huang et al. |
| 2008/0167671 | A1 | 7/2008 | Giordano et al. |
| 2009/0017773 | A1 | 1/2009 | Dupuis et al. |
| 2009/0079387 | A1 * | 3/2009 | Jin ......................... H02J 50/70 320/108 |
| 2010/0114090 | A1 | 5/2010 | Hosier |
| 2011/0071520 | A1 | 3/2011 | Gilbert |
| 2011/0127954 | A1 | 6/2011 | Walley |
| 2011/0204119 | A1 | 8/2011 | McCuen |
| 2011/0208170 | A1 | 8/2011 | Hafner et al. |
| 2011/0248668 | A1 | 10/2011 | Davis et al. |
| 2013/0075443 | A1 | 3/2013 | Giordano et al. |
| 2013/0079790 | A1 | 3/2013 | Stein et al. |
| 2013/0236192 | A1 | 9/2013 | Deicke |
| 2015/0088115 | A1 | 3/2015 | Smith |

FOREIGN PATENT DOCUMENTS

| | | |
|---|---|---|
| JP | 2000332648 A | 11/2000 |
| JP | 2004135245 A | 4/2004 |
| JP | 2011067631 A | 4/2011 |
| JP | 2012187408 A | 10/2012 |
| JP | 2015523848 A | 8/2015 |
| WO | 2008017041 A2 | 2/2008 |

OTHER PUBLICATIONS

Japanese Office Action dated Sep. 20, 2017, for JP Application No. 2016-238594 with English Translation (40 pages).
Japanese Office Action dated May 30, 2018 in corresponding Japanese Patent Application No. 2016-238594 with English translation.
European Search Report from corresponding EP 14186187.2 dated Feb. 16, 2015.

* cited by examiner

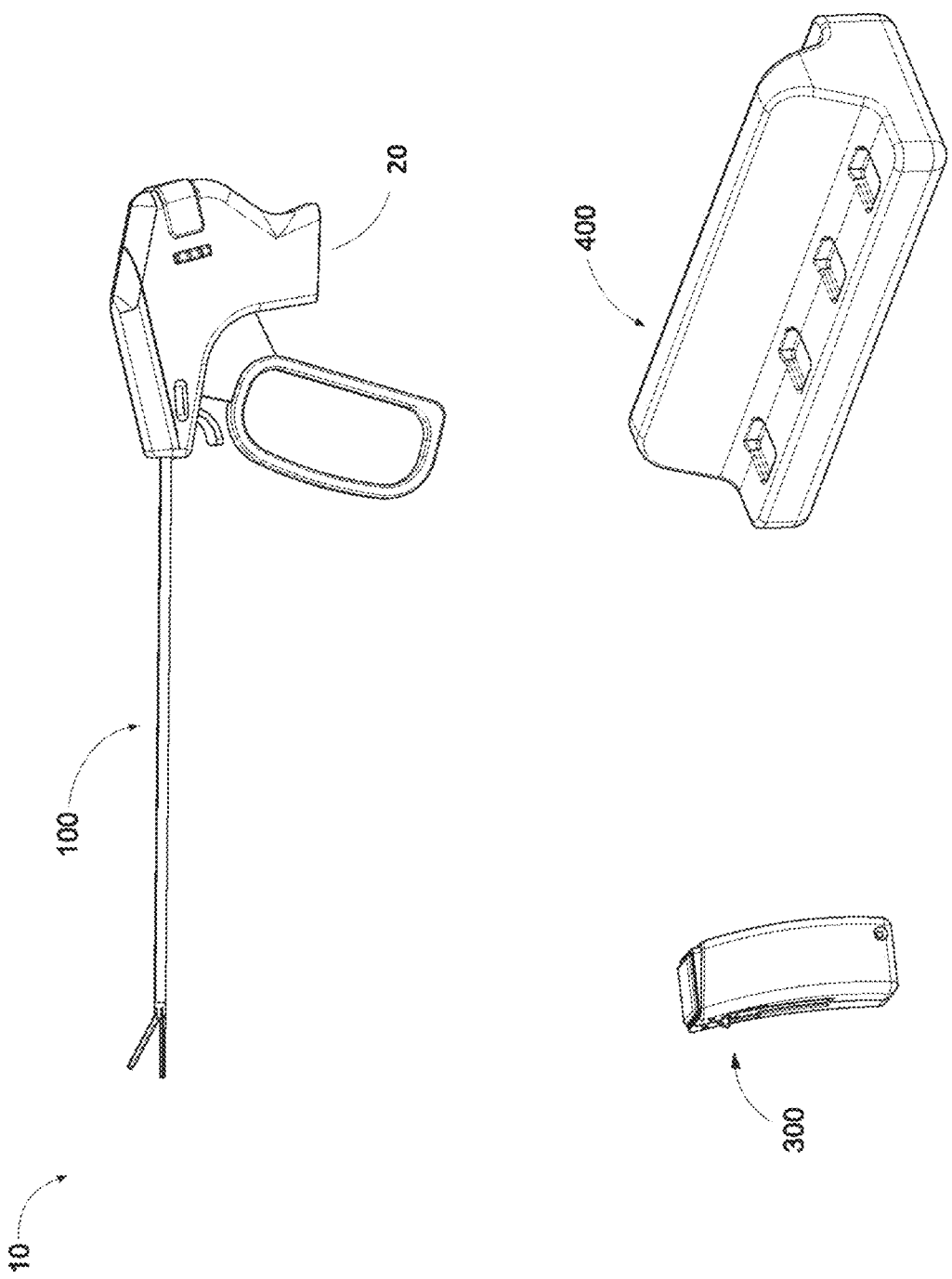

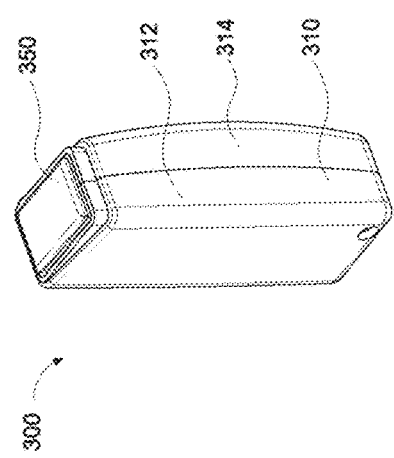
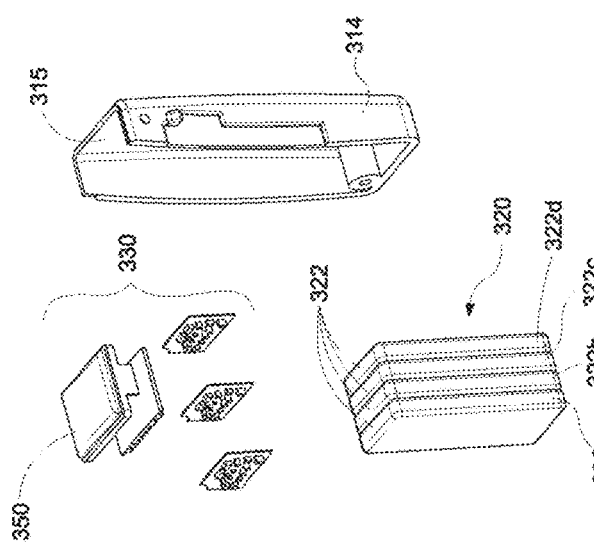
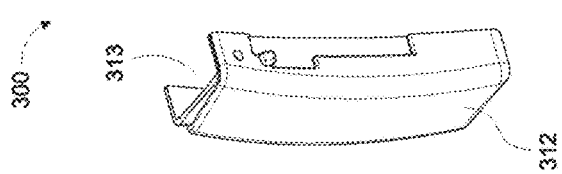

POWER AND BI DIRECTIONAL DATA INTERFACE ASSEMBLY AND SURGICAL SYSTEM INCLUDING THE SAME

CROSS REFERENCE TO RELATED APPLICATIONS

This application is a continuation of U.S. patent application Ser. No. 14/966,832, filed on Dec. 11, 2015, which is a continuation-in-part of U.S. patent application Ser. No. 14/259,819, filed on Apr. 23, 2014, now U.S. Pat. No. 8,872,723, which claims the benefit of the filing date of provisional U.S. Patent Application No. 61/881,536, filed on Sep. 24, 2013.

INTRODUCTION

The present disclosure relates to a power and bi-directional data interface assembly and a surgical system including the same.

BACKGROUND

Operation of energy-based surgical devices typically requires that power and data be transferred between the energy source circuitry and the surgical instrument. For instance, it may be desirable to have hand switch closure detection, return energy pad monitoring, and/or control data and/or signals be communicated between the energy source circuitry and the surgical instrument. One technical challenge in doing so, however, is that energy-based surgical systems typically include an isolation boundary between the patient and the energy source to isolate the patient from potentially dangerous voltage and/or current levels.

In view of the above, there is a need for an improved system for effective and efficient transfer of power and data in both directions, across the isolation boundary, between an energy source and a surgical instrument.

SUMMARY

According to an aspect of the present disclosure, a surgical system is provided that includes a power supply, a surgical instrument, and a power and data interface assembly. The power and data interface assembly include a transformer having a primary winding and a secondary winding, a first modulator coupled to the primary winding and configured to receive a power signal from the power supply, a first demodulator coupled to the secondary winding, a second modulator coupled to the secondary winding, a second demodulator coupled to the primary winding, and at least one capacitor configured to tune the primary winding to a first resonant frequency and tune the secondary winding to a second resonant frequency different than the first resonant frequency.

In another aspect of the present disclosure, the transformer is an air core transformer.

In another aspect of the present disclosure, the first resonant frequency is within a range of 200 kilohertz to 1 gigahertz.

In another aspect of the present disclosure, the second resonant frequency is within a range of 200 kilohertz to 1 gigahertz.

In another aspect of the present disclosure, power from the power signal is delivered to the surgical instrument via the transformer.

In another aspect of the present disclosure, the first demodulator is configured to demodulate, according to the first type of modulation, the modulated power signal to obtain the first data and communicate the first data to a second processor. The second demodulator is configured to demodulate, according to the second type of modulation, the modulated second signal to obtain the second data, and communicate the second data to a first processor.

In another aspect of the present disclosure, the first data is generated by the first processor and includes control information for controlling the surgical instrument, and the second data is generated by the second processor based on a sensor signal received from a sensor.

In another aspect of the present disclosure, the sensor includes a hand switch closure detection sensor configured to detect closure of a hand switch of the surgical instrument and/or a return electrode monitoring sensor configured to detect an impedance associated with a return electrode.

In another aspect of the present disclosure, the first type of modulation and the second type of modulation are configured for simultaneous bi-directional communication of the first data and the second data via the transformer.

In another aspect of the present disclosure, the surgical system includes a first processor and a second processor. The first processor is configured to communicate the first data to the second processor via the first modulator, the transformer, and the first demodulator. The second processor is configured to communicate the second data to the first processor via the second modulator, the transformer, and the second demodulator.

In another aspect of the present disclosure, the first type of modulation is phase shift keying modulation, and the second type of modulation is amplitude modulation.

According to another aspect of the present disclosure, a power and data interface assembly is provided that includes a transformer having a primary winding and a secondary winding, a first modulator coupled to the primary winding and configured to receive a power signal from the power supply, a first demodulator coupled to the secondary winding, a second modulator coupled to the secondary winding, a second demodulator coupled to the primary winding, and at least one capacitor configured to tune the primary winding to a first resonant frequency and tune the secondary winding to a second resonant frequency different than the first resonant frequency.

In another aspect of the present disclosure, the transformer is an air core transformer.

In still another aspect of the present disclosure, the first resonant frequency is within a range of 200 kilohertz to 1 gigahertz.

In another aspect of the present disclosure, the second resonant frequency is within a range of 200 kilohertz to 1 gigahertz.

In another aspect of the present disclosure, power from the power signal is delivered to a surgical instrument via the transformer.

In another aspect of the present disclosure, a first demodulator is configured to demodulate, according to a first type of modulation, the modulated power signal to obtain a first data and communicate the first data to a second processor. A second demodulator is configured to demodulate, according to a second type of modulation, the modulated second signal to obtain a second data, and communicate the second data to a first processor.

In another aspect of the present disclosure, the first data is generated by the first processor and includes control information for controlling a surgical instrument. The second data is generated by the second processor based on a sensor signal received from a sensor. The control information may include temperature data, device calibration data, device usage data, force data, and/or orientation data.

In another aspect of the present disclosure, the sensor includes a hand switch closure detection sensor configured to detect closure of a hand switch of a surgical instrument and/or a return electrode monitoring sensor configured to detect an impedance associated with a return electrode.

BRIEF DESCRIPTION OF THE DRAWINGS

Various aspects of the present disclosure are described hereinbelow with reference to the drawings, wherein:

FIG. 1 is a side, perspective view of a surgical system provided in accordance with the present disclosure;

FIG. 3 is a side, perspective view of a battery assembly configured for use with the surgical system of FIG. 1;

FIG. 4 is an exploded, perspective view of the battery assembly of FIG. 3;

DETAILED DESCRIPTION

Figure 5:
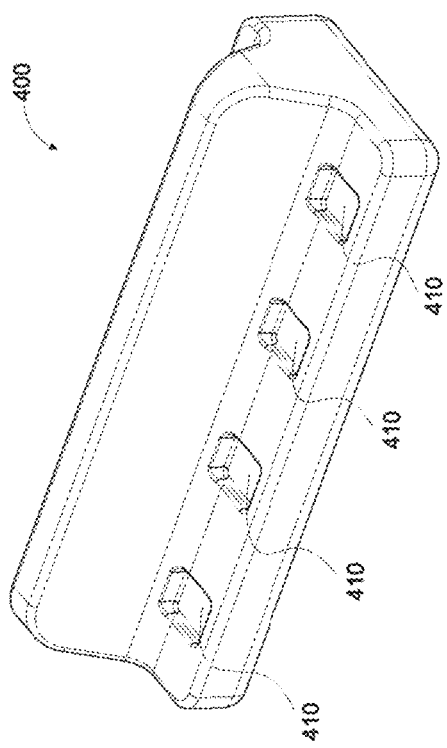
FIG. 5 is a side, perspective view of a battery charger configured for use with the surgical system of FIG. 1.
Figure 6:
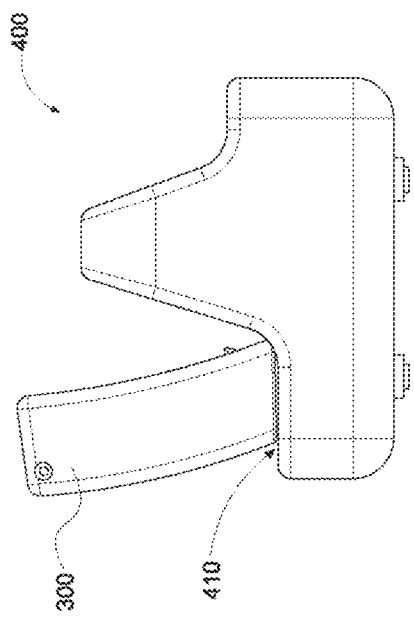
FIG. 6 is a side view of the battery charger of FIG. 5.

Referring now to FIGS. 1-8, a surgical system 10 provided in accordance with the present disclosure generally includes a portable, battery-powered surgical instrument 20, a rechargeable battery assembly 300 (FIGS. 3 and 4), and a battery charger 400 (FIGS. 5 and 6). Surgical system 10 is configured to permit simultaneous bi-directional communication between rechargeable battery assembly 300 and one or more target devices, e.g., surgical instrument 20 and battery charger 400, for example, using phase shifting and amplitude modulation of a power square wave transferred across a transformer. Although phase shifting and amplitude modulation are disclosed with respect to the exemplary embodiments detailed herein, other suitable configurations and/or methods of wireless data transmission are also contemplated. As detailed below, battery assembly 300 is configured to removably couple to both surgical instrument 20 and battery charger 400 in electrical communication therewith via transformers 42 (FIG. 7) and 52 (FIG. 8), respectively, to provide inductive transfer of energy and simultaneous bi-directional communication. Other suitable loads for electrical coupling to battery assembly 300 are also contemplated including, for example, computers, robotic systems, other instruments, etc.

Figure 2A:
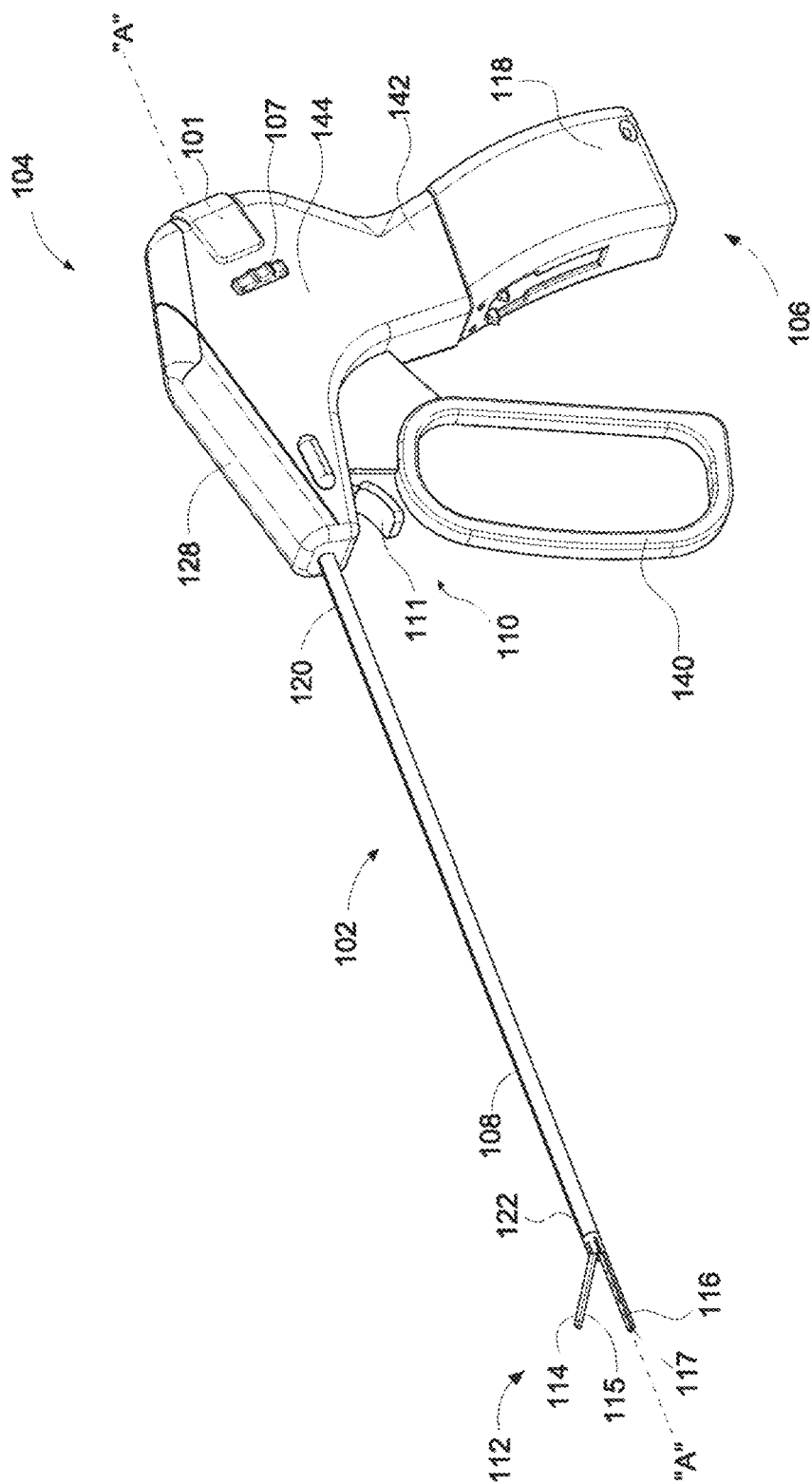
FIG. 2A is a side, perspective view of a portable, battery-powered surgical instrument configured for use with the surgical system of FIG. 1.
Figure 2B:
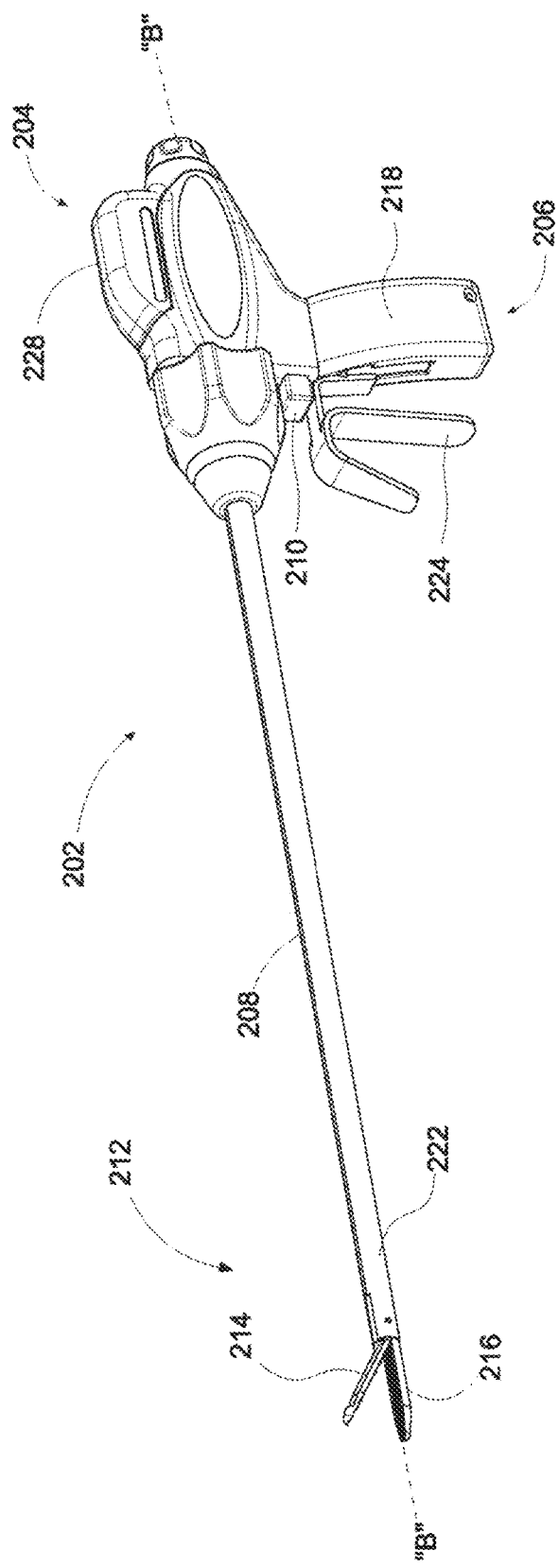
FIG. 2B is a side, perspective view of another portable, battery-powered surgical instrument configured for use with the surgical system of FIG. 1.

Surgical instrument 20 may be for example, a portable, battery-powered electrosurgical instrument 102, as shown in FIG. 2A, a portable, battery-powered ultrasonic surgical instrument 202, as shown in FIG. 2B, or any other suitable battery-powered device such as a handheld tool, electronic device, or the like. As can be appreciated, different considerations apply to each particular type of device; however, the features and aspects of the present disclosure are equally applicable and remain generally consistent with respect to any suitable battery-powered device. For the purposes herein, electrosurgical instrument 102 and ultrasonic instrument 202 are generally described.

With reference to FIG. 2A, electrosurgical instrument 102, shown as an electrosurgical forceps, generally includes a housing 104, a handle assembly 106, a rotating assembly 107, a shaft 108, a trigger assembly 110, a drive assembly (not shown), an end effector assembly 112, a battery assembly 118, and an electrosurgical generator 128. End effector assembly 112 operatively connects to handle assembly 106 via the drive assembly (not shown) for imparting movement of one or both of jaw members 114, 116 of end effector assembly 112 between a spaced-apart position and an approximated position for grasping tissue therebetween.

Continuing with reference to FIG. 2A, shaft 108 is coupled to housing 104 at proximal end 120 thereof and extends distally from housing 104 to define a longitudinal axis "A-A." End effector assembly 112, including jaw members 114 and 116, is disposed at a distal end 122 of shaft 108. End effector assembly 112 is shown configured as a unilateral assembly wherein jaw member 116 is fixed relative to shaft 18 and jaw member 114 is pivotable relative to jaw member 116 and shaft 108 between the spaced-apart and approximated positions. However, this configuration may be reversed, e.g., wherein jaw member 114 is fixed relative to shaft 108 and jaw member 116 is pivotable relative to jaw member 114 and shaft 108. Alternatively, end effector assembly 112 may be configured as a bilateral assembly, e.g., wherein both jaw members 114, 116 are pivotable relative to one another and shaft 8 between the spaced-apart and approximated positions.

Electrosurgical instrument 102 may be configured as a bipolar instrument. That is, each of the jaw members 114, 116 may include a respective seal plate 115, 117 that is configured to function as an active (or activatable) and/or return electrode. Each seal plate 115, 117 is electrically coupled to generator 128 via one or more electrical leads (not shown) that extend from generator 128, through shaft 108, eventually coupling to one or both of seal plates 115, 117 for conducting energy through tissue grasped therebetween. However, forceps 102 may alternatively be configured as a monopolar instrument.

Handle assembly 106 includes a moveable handle 140 that is movable relative to fixed handle portion 142 for moving jaw members 114, 116 of end effector assembly 112 between the spaced-apart and approximated positions. Rotating assembly 107 is rotatable in either direction about longitudinal axis "A-A" to rotate shaft 108 and, thus, end effector assembly 112 about longitudinal axis "A-A." Trigger assembly 110 is in operable communication with a knife assembly (not shown) including a knife blade (not shown) that is selectively translatable between jaw members 114, 116 to cut tissue grasped therebetween, e.g., upon actuation of trigger 111 of trigger assembly 110.

With continued reference to FIG. 2A, housing 104 is configured to releasably engage electrosurgical generator 128 and battery assembly 118. Generator 128 is releasably engagable with body portion 144 of housing 104, while battery assembly 118 is releasably engagable with fixed handle portion 142 of housing 104. More specifically, battery assembly 118 is configured to engage fixed handle portion 142 of housing 104 such that battery assembly 118 functions as the stationary handle of housing 104 to facilitate grasping of the forceps 102. Generator 128 releasably engages body portion 144 of housing 104 and may be selectively removable from body portion 144 either in connection with the removal of battery assembly 118 or independently.

When forceps 102 is assembled, generator 128 is disposed in operable communication with battery assembly 118 to provide electrosurgical energy to end effector 112 for electrosurgically treating tissue, e.g., to seal tissue, although forceps 102 may alternatively be configured to deliver any other suitable form of energy to tissue, e.g., thermal energy, microwave energy, light energy, etc. With respect to electrosurgical tissue treatment, generator 128 may include suitable electronics that convert the electrical energy from battery assembly 118 into an RF energy waveform to energize one or both of jaw members 114, 116. That is, generator 128 may be configured to transmit RF energy to seal plate 115 of jaw member 114 and/or seal plate 117 of jaw member 116 to conduct energy therebetween for treating tissue. Activation switch 101 disposed on housing 104 is activatable for selectively enabling generator 128 to generate and subsequently transmit RF energy to seal plate 115 and/or seal plate 117 of jaw members 114, 116, respectively, for treating tissue grasped therebetween.

Referring now to FIG. 2B, ultrasonic instrument 202 includes components similar to that of forceps 102 shown in FIG. 2A, namely, a housing 204, a handle assembly 206, a shaft 208, an end effector assembly 212, a battery assembly 218, and a generator 228. Accordingly, only the differences between ultrasonic instrument 202 and forceps 102 (FIG. 2A) will be described in detail below.

Housing 204 is configured to releasably engage ultrasonic generator 228 and battery assembly 218. Shaft 208 extends distally from housing 204 to define longitudinal axis "B-B" and includes end effector assembly 212 disposed at distal end 222 thereof. One or both of jaw members 214 and 216 of end effector assembly 212 are movable relative to one another, e.g., upon actuation of moveable handle 224, between an open position and a clamping position for grasping tissue therebetween. Further, one of the jaw members, e.g., jaw member 216, serves as an active or oscillating ultrasonic blade that is selectively activatable to ultrasonically treat tissue grasped between jaw members 214, 216.

Generator 228 includes a transducer (not shown) configured to convert electrical energy provided by battery assembly 218 into mechanical energy that produces motion at the end of a waveguide, e.g., at jaw member 216. More specifically, the electronics (not explicitly shown) of the generator 228 convert the electrical energy provided by battery assembly 218 into a high voltage AC waveform that drives the transducer (not shown). When the transducer (not shown) and the waveguide are driven at their resonant frequency, mechanical, e.g., ultrasonic, motion is produced at the active jaw member 216 for treating tissue grasped between jaw members 214, 216. Further, an activation button 210 disposed on housing 204 is selectively activatable to operate instrument 202 in two modes of operation: a low-power mode of operation and a high-power mode of operation.

Referring to FIGS. 3 and 4, features and aspects of the present disclosure are described with respect to exemplary battery assembly 300. The aspects and features of exemplary battery assembly 300 are equally applicable for use with battery assembly 118 (FIG. 2A) of forceps 102 (FIG. 2A), battery assembly 218 (FIG. 2B) of forceps 202 (FIG. 2B), or any other suitable battery assembly configured for use with a battery-powered device.

Battery assembly 300 generally includes an outer housing 310, a battery pack 320, battery circuitry 330, and an interface cap 350. Outer housing 310 is formed from first and second housing parts 312, 314 that cooperate to house battery pack 320 and battery circuitry 330. Housing parts 312, 314 define cut-outs 313, 315, respectively, that cooperate to form a window configured to retain interface cap 350. In some embodiments, first and second housing parts 312, 314 and interface cap 350 may be monolithically formed about battery pack 320 and battery circuitry 330 for example, by overmolding or the like. Battery assembly 300 may be hermetically sealed to inhibit chemical and fluid ingress into the battery assembly during use or sterilization.

With continued reference to FIG. 4, battery pack 320 includes one or more battery cells 322, e.g., lithium polymer battery cells or other suitable battery cells, and, in some embodiments, four battery cells 322a, 322b, 322c, and 322d, although greater or fewer battery cells 322 are also contemplated. Battery cells 322 provide DC voltage to battery circuitry 330 which converts the DC voltage to AC voltage for output across transformers 42 (FIG. 7) and 52 (FIG. 8), as will be detailed below.

Referring now to FIGS. 5 and 6, battery charger 400 includes one or more charging bays 410 for receiving the interface cap 350 of battery assembly 300, and charging circuitry 420 (FIG. 8) configured to transmit and receive power, control signals and/or otherwise communicate with the battery assembly 300 via charging bays 410 when the interface cap 350 is received within one of the charging bays 410.

Figure 7:
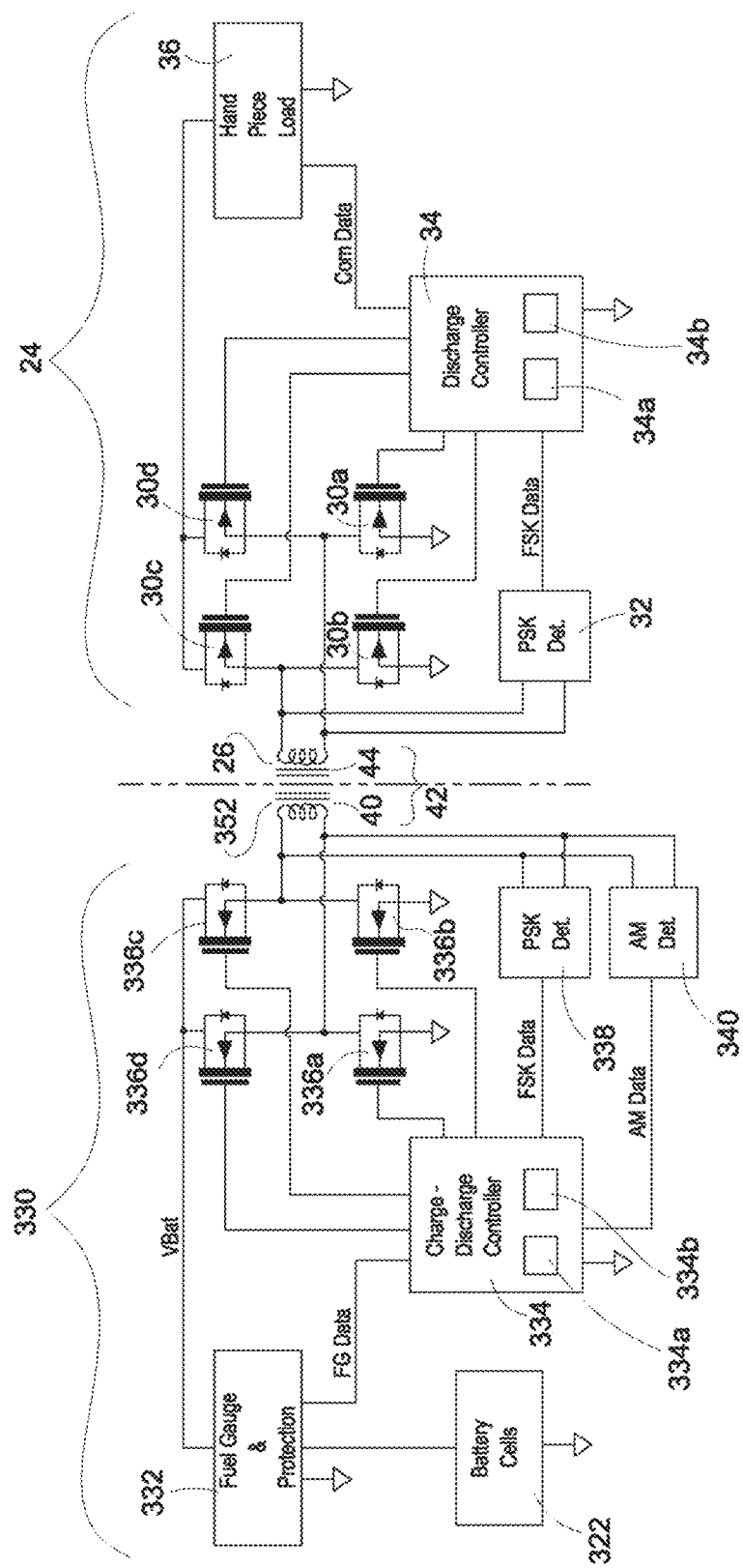
FIG. 7 is a schematic diagram of the circuitry interface between a battery assembly and a surgical instrument in accordance with the surgical system of FIG. 1.
Figure 8:
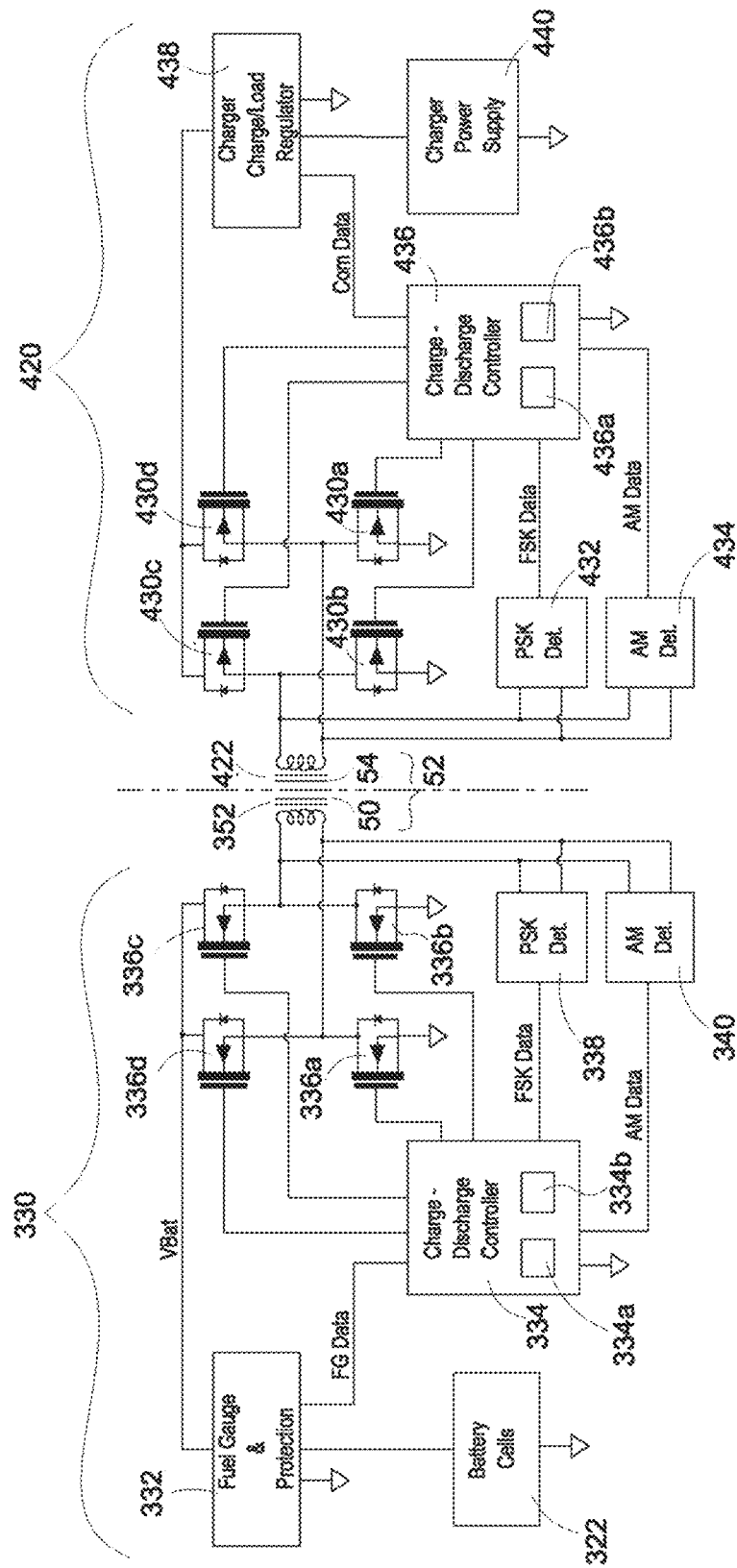
FIG. 8 is a schematic diagram of the circuitry interface between a battery assembly and a battery charger in accordance with the surgical system of FIG. 1.

Referring now to FIGS. 7 and 8, battery circuitry 330 includes fuel gauge and protection circuitry 332, a charge-discharge controller 334, field effect transistors (FETs) 336a-336d, a phase-shift keying (PSK) detector 338, an amplitude modulation (AM) detector 340, and a primary winding 352. Fuel gauge and protection circuitry 332 monitors various battery parameters, e.g., pack impedance, pack temperature, pack voltage, pack current, average current, state of charge, full charge capacity, etc., and provides various safety features, e.g., over and under voltage protection, over current protection, over and under temperature protection, etc. Fuel gauge and protection circuitry 332 also communicates with charge-discharge controller 334 to control the charging and discharging of battery cells 322 across transformers 42 (FIG. 7) and 52 (FIG. 8) via primary winding 352, and provides relevant fuel gauge data, e.g., regarding the state, condition, and/or parameters of battery assembly 300, for transmission across transformers 42 (FIG. 7) and 52 (FIG. 8) via primary winding 352.

Charge-discharge controller 334 includes a processor 334a and memory 334b, e.g., ROM, RAM, or other suitable memory for temporarily or permanently storing information received by controller 334. Charge-discharge controller 334 is configured to communicate with a target device, e.g., a surgical instrument 100 (FIGS. 1 and 2) or a charger 400 (FIGS. 5 and 6), via primary winding 352 as needed to control the transmission and reception of energy for discharging or charging the battery pack 320.

Primary winding 352 is electrically connected to fuel gauge and protection circuitry 332, charge-discharge controller 334, FETs 336a-336d, phase-shift keying (PSK) detector 338, amplitude modulation (AM) detector 340, and battery cells 322. Interface cap 350 includes primary winding 352 which is configured as a first winding 40 (FIG. 7) of a transformer 42 (FIG. 7) to provide an inductive, e.g., wireless, electrical interface between battery assembly 300 and a surgical instrument 20, e.g., electrosurgical instrument 102 (FIG. 1) or ultrasonic instrument 202 (FIG. 2), for transmitting or receiving power, data, and/or control signals therebetween. Primary winding 352 is also configured as a first winding 50 (FIG. 8) of a transformer 52 (FIG. 8) to provide an inductive, e.g., wireless, electrical interface between battery assembly 300 and charger 400 (FIGS. 5 and 6) for transmitting or receiving power, data, and/or control signals therebetween.

FETs 336a-336d are configured in a full bridge topology (although other suitable configurations are also contemplated) to convert the DC voltage from battery cells 322 to AC voltage for output across transformers 42 (FIG. 7) and 52 (FIG. 8) for discharging the battery cells 322 and to convert incoming AC voltage across transformer 52 (FIG. 8) to DC voltage for charging the battery cells 322. For example, FETs 336a-336d are alternately switched on and off in pairs, 336a, 336b and 336c, 336d to generate a power square wave output across transformer 42. FETs 336a-336d may be switched on and off according to clock cycles of the processor 334a of charge-discharge controller 334.

Referring now to FIG. 7, surgical instrument 20 (FIG. 1) includes a battery dock 22 (FIG. 1) configured to receive battery assembly 300 and having device circuitry 24. Device circuitry 24 includes a secondary winding 26 configured as a second winding 44 of transformer 42 when battery assembly 300 is inserted into battery dock 22. Battery dock 22 is configured to receive battery assembly 300 such that primary winding 352 of interface cap 350 aligns with secondary winding 26 of device circuitry 24 to form transformer 42. Battery dock 22 and/or interface cap 350 may include an insulative barrier to insulate the primary and secondary windings 352 and 26 from direct electrical contact, i.e., establishing wireless electrical communication therebetween.

Device circuitry 24 includes a plurality of FETs 30a-30d, a PSK detector 32, and a discharge controller 34. Discharge controller 34 includes a processor 34a and memory 34b similar to charge-discharge controller 334. Secondary winding 26 is electrically connected to FETs 30a-30d, PSK detector 32, and discharge controller 34 which are in turn electrically connected to a hand piece load 36.

FETs 30a-30d are configured in a full bridge topology (although other suitable configurations are also contemplated) to rectify the AC voltage input from transformer 42 to DC voltage for use by the hand piece load 36. For example, FETs 30a-30d are alternately switched on and off in pairs, 30a, 30c and 30b, 30d, to convert the power square wave to DC voltage. FETs 30a-30d may be switched on and off according to clock cycles of the processor 34a of discharge controller 34.

Hand piece load 36 may be any load used by a hand-held surgical device including, for example, an electrosurgical or ultrasonic generator, a motor, control buttons or switches, or other similar hand piece loads 36.

As detailed below, in addition to enabling power transfer from battery assembly 300 to surgical instrument 20, battery circuitry 330 of battery assembly 300 is further configured to perform simultaneous bi-directional communication with device circuitry 24 by using both phase shifting and amplitude modulation on the transferred power square wave signal. That is, by using these two different communication methods, e.g., phase shifting and amplitude modulation, simultaneous bi-directional communication can be achieved. However, although the exemplary embodiments are detailed below with respect to a configuration wherein data transfer from the battery circuitry 330 to the device circuitry 24 is accomplished through phase shifting and wherein data transfer from the device circuitry 24 to the battery circuitry 330 is accomplished through AM modulation, it is also contemplated that this configuration be reversed or that other suitable communication methods be provided for enabling simultaneous bi-directional communication.

During power transfer from battery assembly 300 to surgical instrument 20, charge-discharge controller 334 converts the DC battery voltage from battery cells 322 into an AC power square wave for output across transformer 42 by using FETs 336a-336d as described above. The power square wave may have a frequency of 200 KHz, although other suitable frequencies or frequency ranges are also contemplated, depending on a particular application. For example, low power transfer applications may use higher frequencies to reduce the size of the circuit components, particularly of the transformer. High power transfer applications, on the other hand, may require or desire lower frequencies in order to improve efficiency and/or reduce heating within the battery pack and/or at the hand piece load 36. The discharge controller 34 of device circuitry 24 initially receives power via passive full bridge rectification of the incoming power from transformer 42 and, once initialized, uses FETs 30a-30d to rectify the incoming power with the load 36 and to convert the incoming power back to DC voltage for output to the hand piece load 36, e.g., the generator of the surgical instrument 20. PSK detector 32 functions to monitor the incoming power square wave from transformer 42 to detect if the hand piece load 36 and the incoming power square wave are out of sync. PSK detector 32 also causes the FETs 30a-30d to rectify the phase of the received power square wave to be synchronized with the hand piece load 36 when the incoming power square wave and the hand piece load 36 are out of sync. Data transfer from the battery circuitry 330 to the device circuitry 24 is accomplished through phase shifting of the power square wave. For example, charge-discharge controller 334 of battery circuitry 330 communicates with fuel gauge 332 to obtain fuel gauge data and transmits the fuel gauge data across transformer 42 by phase shifting the power square wave. The PSK detector 32 of device circuitry 24 monitors, cycle by cycle, the incoming power square wave from transformer 42 to detect a phase shift and decodes the data from the phase shift for passing on to the discharge controller 34 for interpretation. As an example, if PSK detector 32 detects an incoming power square wave that is synchronized with the hand piece load 36, the PSK detector 32 outputs a binary output of "0" to discharge controller 34 while if PSK detector 32 detects an incoming power square wave that is phase shifted relative to the hand piece load 36, the PSK detector 32 outputs a binary output of "1" to controller 34. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the battery circuitry 330 and the device circuitry 24 if the power square wave is synchronized with the output load 36, or outputting other values or indicators of the data being extracted to discharge controller 34. To ensure that the phase shifting of the power square wave is properly detected, the clock timing of the charge-discharge controller 334 and the discharge controller 34 may be synchronized upon initialization of power transfer across transformer 42.

Data transfer from the device circuitry 24 to the battery circuitry 330 is accomplished through AM modulation of the power square wave transferred across transformer 42. For example, incoming power load requirements from the handpiece load 36 can be varied, cycle by cycle, by turning the synchronizing FETs 30a-30d on and off at the power square wave frequency to modulate the resulting current draw and therefore the amplitude of the power square wave output from battery circuitry 330 across transformer 42. By varying the cycle by cycle load requirements, the amplitude of the outgoing power square wave from the battery circuitry 330 side of transformer 42 can be controlled by the device circuitry 24 and data can be transferred from the device circuitry 24 to the battery circuitry 330. The AM detector 340 decodes the data from the changes in amplitude caused by the device circuitry 24 for passing on to the charge-discharge controller 334 for interpretation. For example, detection of an initial or baseline amplitude of the power square wave by AM detector 340 results in an output of a binary "0" to charge-discharge controller 334 while detection of an increased or decreased amplitude by AM detector 340 results in an output of a binary "1" to charge-discharge controller 334. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the device circuitry 24 and the battery circuitry 330 if the power square wave has the baseline or initial amplitude, or outputting other values or indicators of the data being extracted to charge-discharge controller 334.

During power supply to hand piece load 36, the amplitude of the power square wave may also be modulated by natural fluctuations in the power requirements of the load. To ensure that the data being transferred through amplitude modulation of the power square wave is properly detected, some form of frequency discrimination between the natural power load fluctuations and the desired data modulation is necessary. For example, the power square wave may be used as a data clock to discriminate between the natural load power fluctuations and the desired data modulation. During the transfer of power, the natural load power fluctuations from the hand piece load 36 of the surgical device 20 will typically be an order of magnitude lower in frequency than the cycle to cycle modulation produced by the AM modulation of the power square wave, thus enabling discrimination. Various high pass/low pass filters or tracking mechanisms (not shown) may be employed to adequately discriminate between the low frequency load fluctuations and the high frequency AM data modulation.

Referring now to FIG. 8, charging circuitry 420 of battery charger 400 (FIG. 1) includes a secondary winding 422 within each charging bay 410 configured as a second winding 54 of transformer 52 when battery assembly 300 is inserted into a charging bay 410. Charging bay 410 is configured to receive battery assembly 300 such that primary winding 352 of interface cap 350 aligns with secondary winding 422 of battery charger 400 to form transformer 52.

Charging circuitry 420 includes a plurality of FETs 430a-430d, a PSK detector 432, and AM detector 434, a charge-discharge controller 436, and a charger charge/load regulator 438. Charge-discharge controller 436 includes a processor 436a and memory 436b similar to charge-discharge controller 334. Secondary winding 422 is electrically connected to FETs 430a-430d, PSK detector 432, AM detector 434, charge-discharge controller 436, and charger charge/load regulator 438. Charger charge/load regulator 438 is in turn electrically connected to a charger power supply 440 which is in turn connected to a source of electrical energy such as, for example, a wall outlet (mains supply). Charger power supply 440 provides a DC voltage to charging circuitry 420.

Charger 400 and battery circuitry 330 cooperate to enable charging and discharging of battery cells 322 and performance of continuous bi-directional simultaneous communication during both charging and discharging by using both phase shifting and amplitude modulation on the transferred power square wave signal, similarly as detailed above with respect to battery circuitry 330 and surgical instrument 20.

During a charging cycle, power is transferred from charger 400 to battery assembly 300 to charge battery cells 322. Charger 400 receives DC voltage from charger power supply 440 and charge-discharge controller 436 converts the DC voltage from charger power supply 440 into an AC power square wave for output across transformer 52 by using FETs 430a-430d in a similar manner to FETs 336a-336d as described above for battery circuitry 300. The charge-discharge controller 334 of battery circuitry 300 uses FETs 336a-336d to rectify the incoming power square wave back to DC voltage for storing in the battery cells 322. PSK detector 338 functions to monitor the incoming power square wave from transformer 52 to detect if the load from the battery cells 322 and the incoming power square wave are out of sync. PSK detector 338 also rectifies the phase of the received power square wave to be synchronized with the load from the battery cells 322.

Data transfer from the charger circuitry to the battery circuitry 330 during charging of battery cells 322 is accomplished through phase shifting of the power square wave. Alternatively, this data transfer may be accomplished using AM modulation, with the transfer of data from battery circuitry 330 to charger circuitry 420 being accomplished using phase shifting. Charge-discharge controller 436 of charger circuitry 420, for example, communicates with charger charge/load regulator 438 to obtain charging data and transmits the charging data across transformer 52 by phase shifting the power square wave. The PSK detector 338 of battery circuitry 330 monitors the incoming power square wave from transformer 52 to detect the phase shift and decodes the data from the phase shift for passing on to the charge-discharge controller 334 for interpretation. As an example, if PSK detector 334 detects an incoming power square wave that is synchronized with the load of the battery cells 322, the PSK detector 338 outputs a binary output of "0" to charge-discharge controller 334 while if PSK detector 338 detects an incoming power square wave that is phase shifted relative to the load of the battery cells 322, the PSK detector 338 outputs a binary output of "1" to charge-discharge controller 334. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the charger circuitry 420 and the battery circuitry 330 if the power square wave is synchronized with the load of the battery cells 322, or outputting other values or indicators of the data to extracted to charge-discharge controller 334. To ensure that the phase shifting of the power square wave is properly detected, the clock timing of the charge-discharge controller 436 and the charge-discharge controller 334 may be synchronized upon initialization of power transfer across transformer 52.

Data transfer from the battery circuitry 330 to the charger circuitry 420 during charging of battery cells 322 is accomplished through AM modulation of the power square wave transferred across transformer 52 although, as mentioned above, other configurations are also contemplated. Incoming power load requirements from the battery cells 322 can be varied, for example, by turning the synchronizing FETs 336a-336d on and off at the power square wave frequency to adjust the required amplitude of the power square wave output from charger circuitry 420 across transformer 52. By varying the load requirements, the amplitude of the outgoing power square wave from the charger circuitry 420 side of transformer 52 can be controlled by the battery circuitry 330 and data can be transferred from the battery circuitry 330 to the charger circuitry 420. The AM detector 434 decodes the data from the changes in amplitude caused by the battery circuitry 330 for passing on to the charge-discharge controller 436 for interpretation. For example, detection of an initial or baseline amplitude of the power square wave by AM detector 434 results in an output of a binary "0" to charge-discharge controller 436 while detection of an increased or decreased amplitude by AM detector 434 results in an output of a binary "1" to charge-discharge controller 436. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the battery circuitry 330 and the charger circuitry 420 if the power square wave has the baseline or initial amplitude, or outputting other values or indicators of the data being extracted to charge-discharge controller 436.

During a discharge cycle, power is transferred from battery assembly 300 to charger 400 to discharge battery cells 322. Battery circuitry 330 receives DC voltage from battery cells 322 and charge-discharge controller 334 converts the DC voltage from battery cells 322 into an AC power square wave for output across transformer 52 by using FETs 336a-336d as described above for output across transformer 42. The charge-discharge controller 436 of charger circuitry 420 uses FETs 430a-430d to rectify the incoming power square wave back to DC voltage for discharge through charger charge/load regulator 438 and charger power supply 440. PSK detector 432 functions to monitor the incoming power square wave from transformer 52 to detect if the load from the charger charge/load regulator 438 and the incoming power square wave are out of sync. PSK detector 432 also rectifies the phase of the received power square wave to be synchronized with the load from the charger charge/load regulator 438.

Data transfer from the battery circuitry 330 to the charger circuitry 420 during discharging of battery cells 322 is accomplished through phase shifting of the power square wave. Alternatively, this data transfer may be accomplished using AM modulation, with the transfer of data from charger circuitry 420 to battery circuitry 330 being accomplished using phase shifting. Charge-discharge controller 334 of battery circuitry 330, for example, communicates with fuel gauge 332 to obtain fuel gauge data and transmits the fuel gauge data across transformer 52 by phase shifting the power square wave. The PSK detector 432 of charger circuitry 420 monitors the incoming power square wave from transformer 52 to detect the phase shift and decodes the data from the phase shift for passing on to the charge-discharge controller 436 for interpretation. As an example, if PSK detector 432 detects an incoming power square wave that is synchronized with the load of the charger charge/load regulator 438, the PSK detector 432 outputs a binary output of "0" to charge-discharge controller 436 while if PSK detector 432 detects an incoming power square wave that is phase shifted relative to the load of the charger charge/load regulator 438, the PSK detector 432 outputs a binary output of "1" to charge-discharge controller 436. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the battery circuitry 330 and the charger circuitry 420 if the power square wave is synchronized with the load of the charger charge/load regulator 438, or outputting other values or indicators of the data being extracted to charge-discharge controller 436. To ensure that the phase shifting of the power square wave is properly detected, the clock timing of the charge-discharge controller 334 and the charge-discharge controller 436 may be synchronized upon initialization of power transfer across transformer 52.

Data transfer from the charger circuitry 420 to the battery circuitry 330 during discharging of battery cells 322 is accomplished through AM modulation of the power square wave transferred across transformer 52 although, as mentioned above, other configurations are also contemplated. For example, incoming power load requirements from the load of the charger charge/load regulator 438 can be varied by turning the synchronizing FETs 430a-430d on and off at the power square wave frequency to adjust the required amplitude of the power square wave output from battery circuitry 330 across transformer 52. By varying the load requirements, the amplitude of the outgoing power square wave from the battery circuitry 330 side of transformer 52 can be controlled by the charger circuitry 420 and data can be transferred from the charger circuitry 420 to the battery circuitry 330. The AM detector 340 decodes the data from the changes in amplitude caused by the charger circuitry 420 for passing on to the charge-discharge controller 334 for interpretation. For example, detection of an initial or baseline amplitude of the power square wave by AM detector 340 results in an output of a binary "0" to charge-discharge controller 334 while detection of an increased or decreased amplitude by AM detector 340 results in an output of a binary "1" to charge-discharge controller 334. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the charger circuitry 420 and the battery circuitry 330 if the power square wave has the baseline or initial amplitude, or outputting other values or indicators of the data being extracted to charge-discharge controller 334.

Battery assembly 300 includes two rest states and two active states. Battery assembly 300 is initially configured for shipping in a powered down state, also known as a ship mode. In ship mode, the battery assembly 300 is dormant with the fuel gauge 332 shut down and no power provided to the charge-discharge controller 334. Battery assembly 300 may only be activated from ship mode by placing battery assembly 300 in charger 400.

Once battery assembly 300 has been placed in charger 400 the first time, the supply of power from charger to battery assembly 300 "wakes up" battery assembly 300 from the ship mode and, as a result, battery assembly 300 enters a charge mode. In the charge mode, battery assembly 300 is awake and communicating with charger 400 to accept power from charger 400 as described above. When charging is complete or battery assembly 300 is removed from charger 400 (and after expiration of a delay period, in some embodiments), battery assembly 300 enters a sleep mode. Subsequent placement of the battery assembly 300 in charger 400 wakes up the battery assembly 300 from sleep mode and places the battery assembly 300 in either charge or discharge mode depending on the desired function.

In sleep mode, battery assembly 300 is dormant with fuel gauge 332 waking up periodically to check on the status of the battery assembly 300. Unlike a conventional battery assembly which uses electrical contacts to complete a circuit for determining when to wake up, the use of a transformer for power transfer requires periodic pinging of the primary winding 352 to determine if a load is present. To this end, fuel gauge 332 wakes up the charge-discharge controller 334 and asks the charge-discharge controller 334 to check if an external load is present. The charger-discharge controller 334 pings the primary winding 352 to look for a suitable external load such as, for example, handpiece load 36 or the load of charger charge/load regulator 438. If a load is present across transformer 42 or 52, the battery assembly 300 enters a discharge mode. During the discharge mode, the battery assembly 300 is awake and transmits power to the handpiece load 36 or the load of the charger charge/load regulator 438. Other suitable loads for use with battery assembly 300 are also contemplated. If a load is present across transformer 52, the battery assembly 300 may alternatively enter the charge mode as described above.

Figure 9:
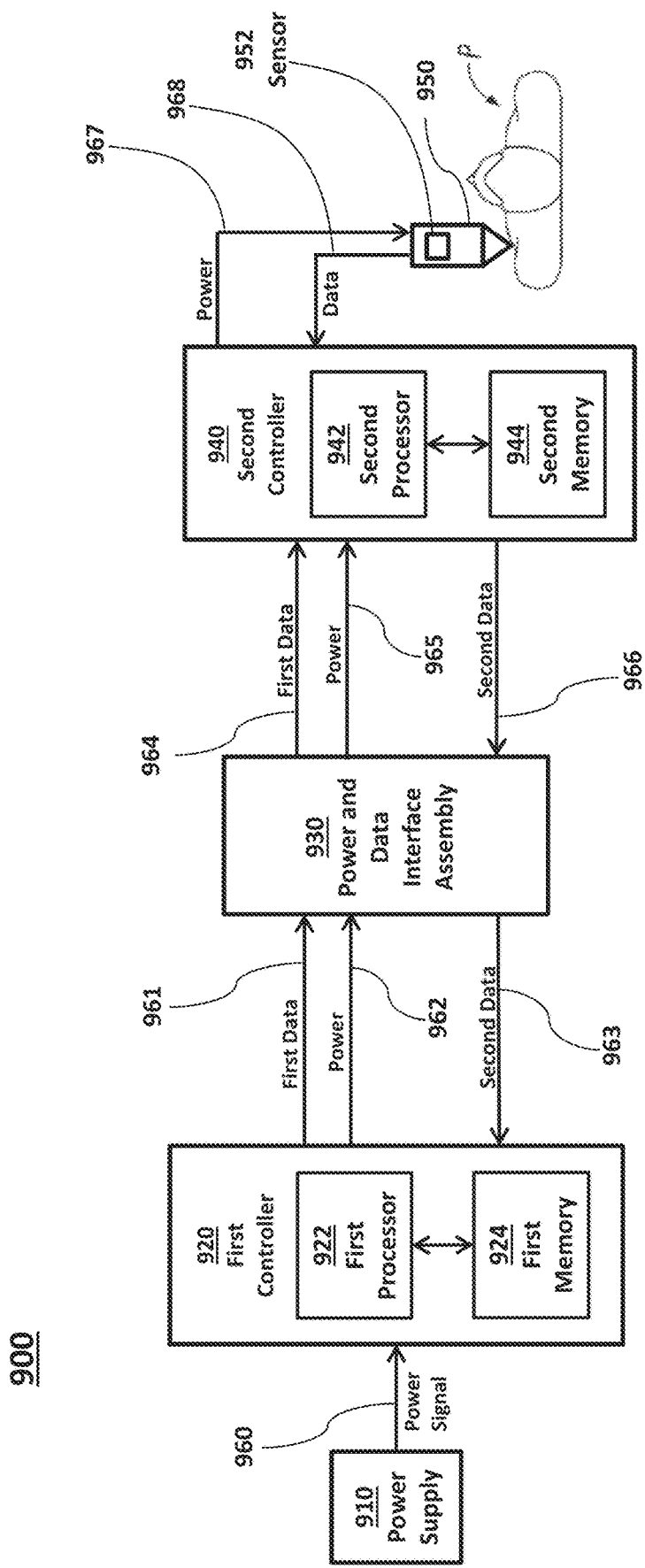
FIG. 9 shows a surgical system in accordance with another example embodiment herein.
Figure 10:
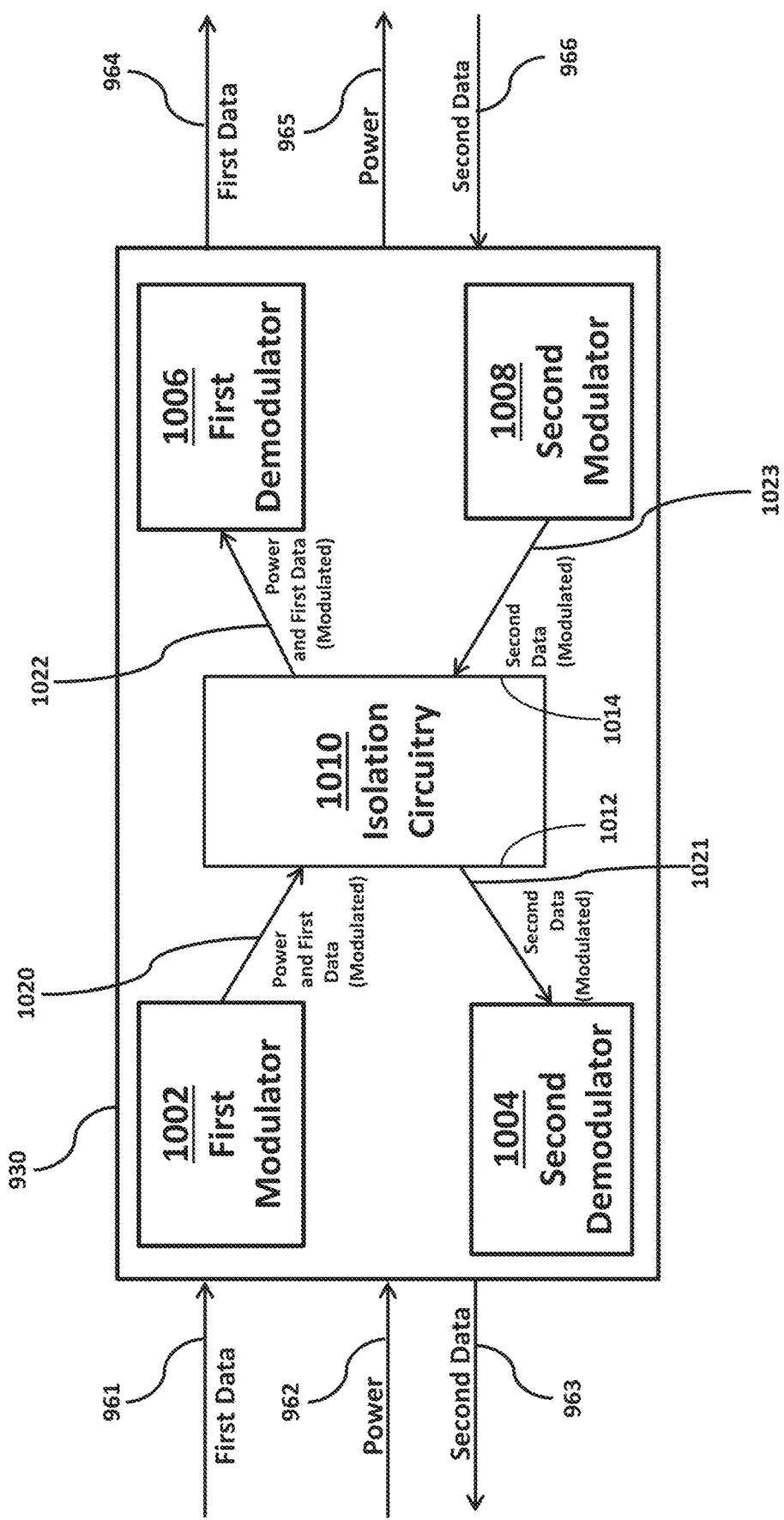
FIG. 10 shows a power and data interface assembly of the surgical system of FIG. 9, in accordance with an example embodiment herein.
Figure 11:
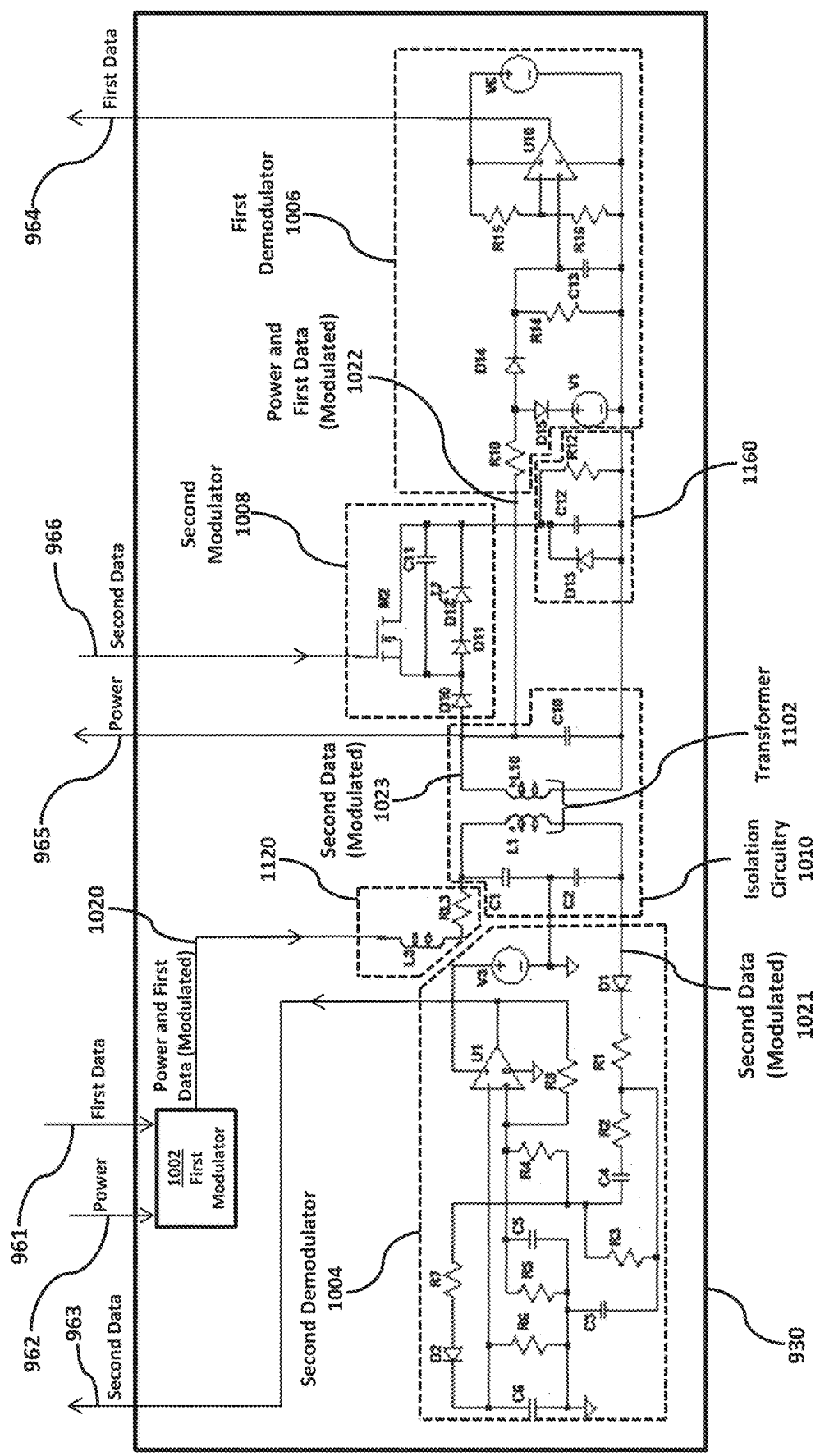
FIG. 11 shows additional aspects of the power and data interface assembly of FIG. 10, in accordance with an example embodiment herein.

Reference will now be made to FIGS. 9, 10, and 11 to describe an example surgical system 900 and a power and data interface assembly 930 included therein, in accordance with another example embodiment herein. In particular, FIG. 9 shows the surgical system 900 and FIGS. 10 and 11 show the power and data interface assembly 930 of the surgical system 900, in accordance with an example embodiment herein. It should be understood that the particular arrangements of components shown in FIGS. 9 through 11 are provided as examples, but other arrangements may be implemented in accordance with the present disclosure. For instance, one or more components of the system 900 may be incorporated into one or more other components of the system 900 (for example, two components, such as the power supply 910, the first controller, the power and data interface assembly 930, and the second controller (described below), may be incorporated into a generator assembly.

As shown in FIG. 9, the surgical system 900 includes a power supply 910, a first controller 920, a power and data interface assembly 930, a second controller 940, and a surgical instrument 950. In general, and as described in further detail below, the system 900 is configured to facilitate the delivery of power (which may also be referred to herein as energy) from the power supply 910 to the surgical instrument 950 (as well as to other components, for instance, to power local circuitry of the first controller 920, the power and data interface assembly 930, and/or the second controller 940), and to facilitate the bidirectional communication of data across an galvanic isolation boundary, which is implemented by the power and data interface assembly 930 (for instance, between the first controller 920, the second controller 940, and/or the surgical instrument 950) to permit the transfer of electrical power while galvanically isolating the patient from potentially dangerous voltage and/or current levels that may exist on the portion of the system 900 having the power supply 910 coupled thereto by way of one or more physical conductors.

In particular, the first controller 920 includes a first processor 922 and a first memory 924 coupled thereto. Together, the first processor 922 and the first memory 924 are configured to implement one or more algorithms relating to the operation of the surgical device 950, such as, for example, generating data (referred to herein as "first data") to be incorporated into a power signal provided thereto by the power supply 910 to be communicated to the second controller 940 and/or to the surgical instrument 950. For instance, a power signal may be transmitted from the power supply 910 to the surgical instrument 950 by way of path 960, the first controller 940, path 962, the power and data interface assembly 930, path 965, the second controller 940, and path 967. The power delivered from the power supply 910 to the surgical instrument 950 may be employed to cause one or more clinical effects to a surgical site, as described above. First data may be transmitted from the first controller 920 to the second controller 940 by way of path 961, the power and data interface assembly 930, and path 964. The first data may be any type of data, such as, by way of example and not limitation, data that is communicated to the surgical instrument 950 to control its operation, feedback data, temperature data, device identification data, device calibration data, device usage data, impedance data, force data, orientation data, and/or any other type of data.

Although FIG. 9 shows various paths as distinct paths, in various embodiments herein, two or more of the paths shown in FIG. 9 may be implemented as one physical path configured to carry multiple data signals and/or power signals simultaneously and/or at different times by utilizing one or more multiplexing and/or modulation techniques. For instance, the path 961 and the path 962 may be implemented as one physical path that carries both power and the first data (for example, by modulating the power signal to include data). Likewise, the path 964 and the path 965 may be realized as one physical path that carries both power and the first data.

The second controller 940 includes a second processor 942 and a second memory 944 coupled thereto. Together, the second processor 942 and the second memory 944 are configured to implement one or more algorithms relating to the operation of the surgical device 950, such as, for example, obtaining data (referred to herein as "second data") from the surgical device 950 by way of path 968, and transmitting the second data to the first controller 920 by way of path 966, the power and data interface assembly 930, and path 963. The second data may be any type of data, such as, by way of example and not limitation, feedback data related to the surgical instrument 950 (sensor data, for example, from a sensor 952, which may be a temperature sensor, a return pad impedance sensor, and/or the like, that is included in the surgical instrument 950).

The surgical instrument 950 may be an electrosurgical instrument that is configured to deliver energy (for example, radio frequency (RF) energy or energy of any other portion on the electromagnetic spectrum) provided by the power supply 910 to a surgical site of a patient, for instance, to cause a clinical effect, such as cutting tissue, coagulating tissue, sealing tissue, and/or the like. Alternatively, the surgical instrument 950 may be an ultrasonic surgical instrument that is configured to vibrate, based on energy provided by the power supply 910, at one or more ultrasonic frequencies to cause a clinical effect at the surgical site of the patient. In general, the power supply 910 may be a battery-based power supply, a generator-based power supply, and/or any other power supply suitable for delivering energy to the surgical instrument 950 and/or to other components of the system 900. In one example embodiment, the power supply 910 may be a battery-based power supply and the surgical instrument 950 may be a battery-powered device, such as, for example, the surgical instrument 20 (FIG. 1), the surgical instrument 102 (FIG. 2A), and/or the surgical instrument 202 (FIG. 2B). In another example embodiment, the power supply 910 may be a generator-based power supply configured to provide energy to the surgical instrument 950. As can be appreciated, different considerations may apply to each particular type of surgical device. However, the features and aspects of the present disclosure are equally applicable and remain generally consistent with respect to any suitable powered surgical device.

Having described the example surgical system 900, reference will now be made to FIG. 10, which shows additional aspects of the power and data interface assembly 930 of the surgical system 900. The power and data interface assembly 930 includes isolation circuitry 1010, having a primary side 1012 and a secondary side 1014, a first modulator 1002, a first demodulator 1006, a second modulator 1008, and a second demodulator 1004. The first modulator 1002 and the second demodulator 1004 are coupled to the primary side 1012 of the isolation circuitry 1010, and the first demodulator 1006 and the second modulator 1008 are coupled to the secondary side 1014 of the isolation circuitry 1010.

The first modulator 1002 receives a power signal from the power supply 910 by way of path 962. The first modulator 1002 is configured to modulate, according to a first type of modulation, the power signal based on first data (for example, as described above), and communicate the modulated power signal to the first demodulator 1006 by way of path 1020, the isolation circuitry 1010, and 1022. The first demodulator 1006 is configured to demodulate, according to the first type of modulation, the modulated power signal to obtain the first data, and communicate the first data to the second controller 940 (and/or to the second processor 942 thereof) by way of path 964.

The second modulator 1008 is configured to modulate, according to a second type of modulation, a second signal (for example, a carrier signal) based on second data, and communicate the modulated second signal to the second demodulator 1004 by way of path 1023, the isolation circuitry 1010, and path 1021. The second demodulator 1004 is configured to demodulate, according to the second type of modulation, the modulated second signal to obtain the second data, and communicate the second data to the first controller 920 (and/or to the first processor 922 thereof) by way of path 1014, the isolation circuitry 1010, and path 1021.

FIG. 11 shows additional aspects of an example embodiment of the power and data interface assembly 930. In particular, example embodiments of the first demodulator 1006, the second modulator 1008, the second demodulator 1004, and the isolation circuitry 1010 are shown in FIG. 11, although in other embodiments, other circuitry and/or topologies may be employed as alternatives to one or another of the components of the assembly 930 (for example, the first demodulator 1006, the second modulator 1008, the second demodulator 1004, and/or the isolation circuitry 1010). Additionally, the power and data interface assembly 930 of FIG. 11 includes a low-pass filter 1120 that filters the modulated power and first data signal received from the first modulator 1002 via path 1020. The example embodiment of the first demodulator 1006 shown in FIG. 11 includes phase detection circuitry followed by comparator circuitry U10 that is configured to square up the demodulated signal. The example embodiment of the second demodulator 1004 shown in FIG. 11 includes diode-implemented peak detection and low pass filtering, followed by comparator circuitry U1 that is configured to square up the demodulated signal.

The isolation circuitry 1010 includes a transformer 1102 having a primary winding L1 and a secondary winding L10. In some example embodiments, may be an air core transformer, such as a radio frequency (RF) air core transformer. The transformer 1102 and/or other components of the assembly 930 may be implemented as a daughter card in some example embodiments, for instance, included within a generator assembly. This configuration may yield relatively low primary-to-secondary capacitance, high voltage isolation which can be provided by an increased primary-to-secondary insulation spacing, small physical size, and effective data and power coupling. Further, the circuitry on the secondary, isolated side of the transformer 1102 may be powered by a relatively small amount of power (for instance, only about 5 or 6 watts). The power delivered to the secondary winding L10 may be rectified and stored on capacitor C10 or another storage element, and the stored voltage may be regulated by a zener diode D13, a voltage regulating integrated circuit (IC), or another voltage regulator.

The transformer 1102 defines the isolation boundary described above in that galvanic isolation is provided between the primary winding L1—to which circuitry on a first side (a power side, for example) of the isolation boundary is coupled—and the secondary winding L10—to which circuitry on a second side (a patient side, or isolated side, for example) of the isolation boundary is coupled. The transformer 1102 is configured to provide galvanic isolation between the first side of the isolation boundary and the second side of the isolation boundary, such that no direct conduction path is provided between the first side and the second side, but also to enable energy and/or data to be exchanged across the isolation boundary by way of capacitance, induction electromagnetic waves, and/or another suitable means. In this way, power and/or energy may be provided by the power supply 910 to the surgical instrument 950 by way of the transformer 1102, while maintaining galvanic isolation between the patient and the power supply 910.

When employing an RF air core transformer as the transformer 1102, the efficiency of power transfer by way of alternating current (AC) signals at frequencies at or below the resonant frequency of the transformer 1102 (and/or the resonant frequencies of the primary winding L1 and the secondary winding L10 thereof) may be greater that the efficiency of power transfer by way of AC signals above those resonant frequencies. Power transfer efficiency is maximum at the resonant frequency of the transformer 1102. Improvements can be obtained by adding a known fixed capacitances to both the primary, and secondary windings. In one example embodiment, the isolation circuitry 1010 also includes tuning circuitry including capacitors C1, C2, and/or C10 that are configured to tune the primary winding L1 (in the case of capacitors C1 and/or C2) or the secondary winding L10 (in the case of capacitor C10) to one or more respective resonant frequencies, which may lower and/or stabilize the resonant frequency of the transformer 1102 (and/or the resonant frequencies of the primary winding L1 and the secondary winding L10 thereof). In one example embodiment, the one or more resonant frequencies are within a range of 200 kilohertz (kHz) to 1 gigahertz (GHz), with higher resonant frequencies enabling greater data transfer bandwidth than lower resonant frequencies. The added capacitances C1, C2, and/or C10 also may increase circulating currents flowing in both halves of the transformer 1102 which may further improve energy transfer. Further, the added capacitances C1, C2, and/or C10 can also be used to set and stabilize the quality factor (Q) of the resulting tuned isolation circuitry 1010. By stabilizing and/or controlling the Q of the isolation circuitry 1010, a smoother RF amplitude and phase may be effected, which is less sensitive to secondary load variations. This may facilitate stable modulation for data transfer across the isolation boundary. In one example, as shown in FIG. 11, a zener diode D13 may be configured to further stabilize the load seen by the secondary winding L10 of the transformer 1102 by absorbing any current not needed by downstream circuitry. In other example embodiments, other methods may be employed to stabilize the Q of the isolation circuitry 1010.

The magnetic coupling coefficient for an air core transformer 1102 with large winding to winding spacing may be significantly less than unity. A lower coupling coefficient can be used to provide primary to secondary voltage and current ratios that do not match actual physical turns ratios. Secondary voltage and/or current may be increased or decreased by tuning the primary winding L1 and the secondary winding L10 to slightly different resonant frequencies. In one example, the capacitors C1 and/or C2 are configured to tune the primary winding L1 to a first resonant frequency and the capacitor C10 is configured to tune the secondary winding L10 to a second resonant frequency, the first resonant frequency being different from the second resonant frequency. Such tuning may be employed to modify primary to secondary data and power transfer characteristics to obtain specific desired results.

With reference to FIGS. 9 through 11, the first processor 922 may be configured to communicate the first data (described above) to the second processor 942 by way of path 961, the first modulator 1002, path 1020, the transformer 1102, path 1022, the first demodulator, and path 964. Likewise, the second processor 942 may be configured to communicate the second data (described above) to the first processor 922 by way of path 966, the second modulator 1008, path 1023, the transformer 1102, path 1021, the second demodulator 1004, and path 963. The first data, which is described in further detail above, may be generated by the first processor 922 and may include control information for controlling the surgical instrument. The second data, which is described in further detail above, may be generated by the second processor 942 based on a sensor signal received from the sensor 952 by way of path 968. In some example embodiments herein, the sensor 952 may include a hand switch closure detection sensor configured to detect closure of a hand switch of the surgical instrument 950, a return electrode monitoring sensor configured to detect an impedance associated with a return electrode (for example, for embodiments where the surgical instrument 950 is a monopolar electrosurgical instrument), a temperature sensor, a mechanical force sensor, and/or any other type of sensor.

As described above in the context of FIGS. 9 through 11, the first data and the second data are modulated according to a first type of modulation and a second type of modulation, respectively, and the first type of modulation and the second type of modulation are configured to facilitate bi-directional communication (which may or may not be simultaneous) of the first data and the second data by way of the transformer 1102. In one example embodiment, the first type of modulation is phase shift keying (PSK) modulation and the second type of modulation is amplitude modulation (AM), although other types of modulation may be employed in various other embodiments. Reference will now be made to FIGS. 12, 13, 14, and 15, which illustrate aspects of the first and second types of modulation, in accordance with an example embodiment herein.

Figure 12:
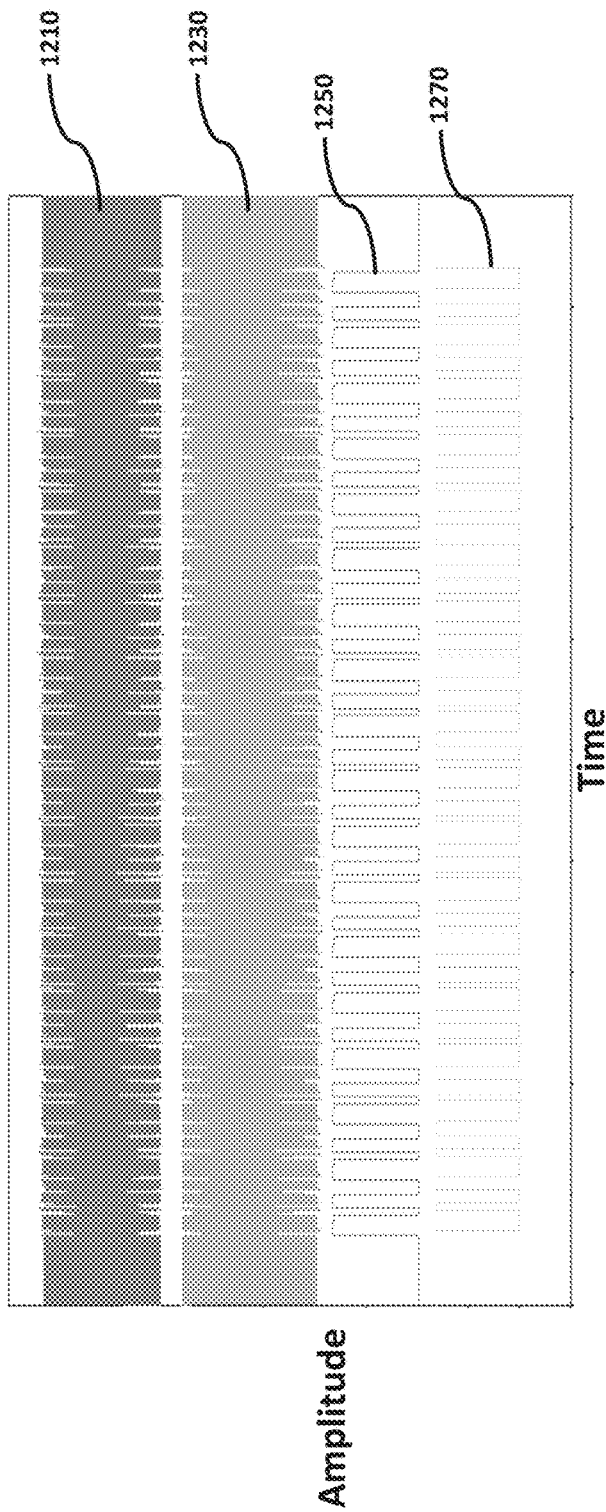
FIG. 12 illustrates phase shift keying (PSK) modulation and demodulation, in accordance with an example embodiment herein.

FIG. 12 illustrates one example of how phase shift keying (PSK) modulation and demodulation may be employed, in accordance with an example embodiment herein. In this example, PSK modulation is employed by the first modulator 1002 to transfer first data from the primary winding L1 to the secondary winding L10 by shifting a carrier signal (for example, a 3 megahertz (MHz) carrier signal) to represent digital values (for example, ones and zeros). This can be implemented, for instance, by inverting (in the case of ones) or not inverting (in the case of zeros) a digital signal coupled to the input power signal from path 960 based on the values of the first data. The phase reversal may then be detected on the patient side of the isolation barrier (for instance, by the first demodulator 1006) such that the first data can be reconstructed. Phase modulation (not necessarily to scale) is depicted in FIG. 12, where the waveform 1250 represents the first data values to be input to the first modulator 1002 and based upon which the 3 MHz carrier signal (not shown separately in FIG. 12) is to be phase shifted. The waveform 1210 represents the phase shifted carrier 3 MHz carrier signal including the first data which is provided to the primary winding L1. The waveform 1230 represents the resulting phase shifted signal as it may appear at the secondary winding L10. The waveform 1270 represents the demodulated first data signal as obtained by the first demodulator 1006 and forwarded by way of path 964.

Figure 13:
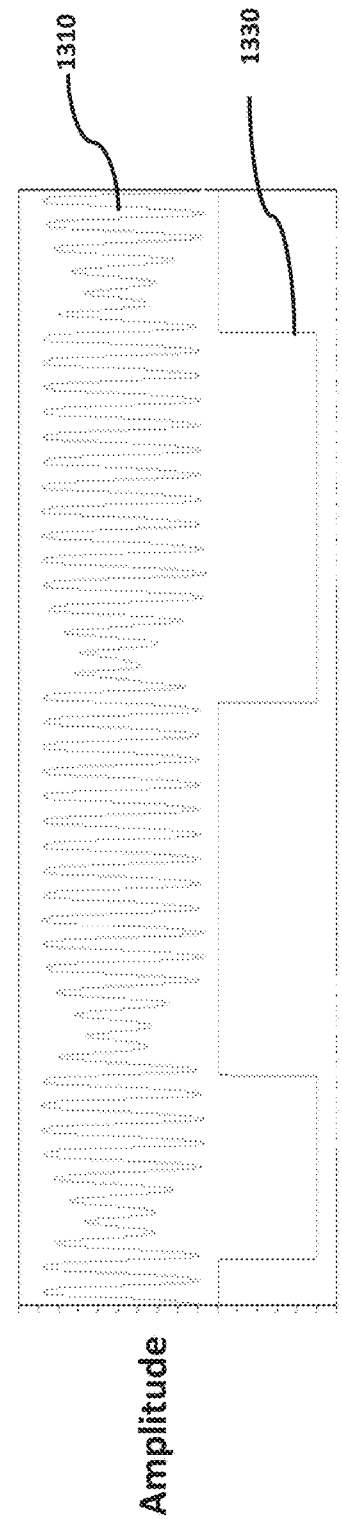
FIG. 13 illustrates reversal of a carrier phase in PSK modulation, in accordance with an example embodiment herein.

To illustrate reversal of a carrier phase in PSK modulation, in accordance with an example embodiment herein, FIG. 13 shows a zoomed in view of a portion of the waveforms 1210 and 1250 that are shown in FIG. 12. In particular, waveforms 1310 and 1330 represent zoomed in portions of the waveforms 1210 and 1250, respectively. The phase of the waveform 11310 during the low voltage (for example, zeros) portions of the waveform 1330 is shifted with respect to the phase of the waveform 11310 during the high voltage (for example, ones) portions of the waveform 1330.

Figure 14:
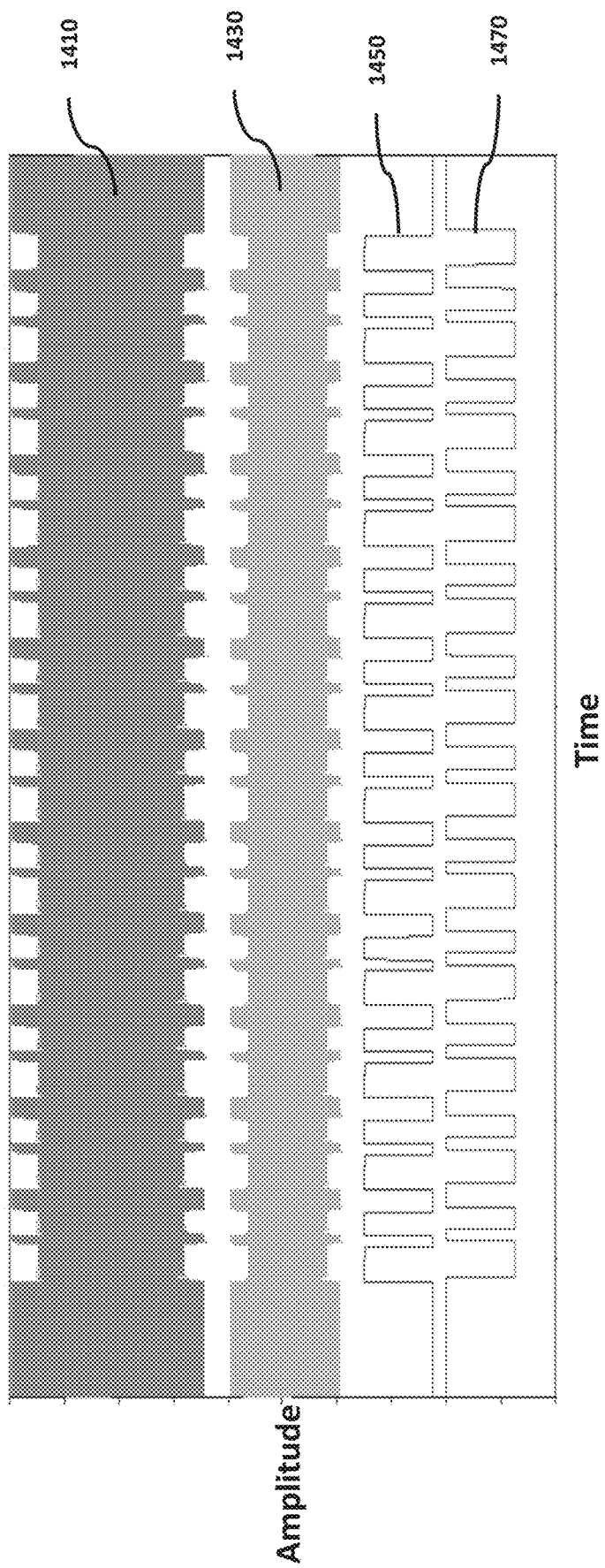
FIG. 14 illustrates amplitude modulation (AM) and demodulation, in accordance with an example embodiment herein.

FIG. 14 illustrates how amplitude modulation (AM) and demodulation may be employed, in accordance with an example embodiment herein. In this example, AM modulation is employed by the second modulator 1008 to transfer second data from the secondary winding L10 to the primary winding L1 by varying the amplitude of a carrier signal (for example, a 3 MHz carrier signal) to represent digital values (for example, ones and zeros). This may be accomplished by employing a field effect transistor (FET) M2 to switch a series voltage drop, provided by diodes D11 and D12, into and out of a current path that feeds a secondary power supply capacitor (for example, capacitor C10, C11, and/or C12) and a voltage regulator (for example, diode D13). The polarity of a signal (for example, conveyed via path 966) driving the FET M2 drive signal may be inverted to provide more efficient power transfer depending on data transfer density. One example of such amplitude modulation (not to scale) is depicted in FIG. 14, where the waveform 1450 represents the drive signal of the modulation FET M2, the waveform 1430 represents the resulting secondary modulation signal (including the second data) provided to the secondary winding L10, the waveform 1410 represents the modulation signal as detected at the primary winding L1 of the transformer 1102, and the waveform 1470 represents the demodulated second data obtained by the second demodulator 1004 and forwarded by way of path 963.

Figure 15:
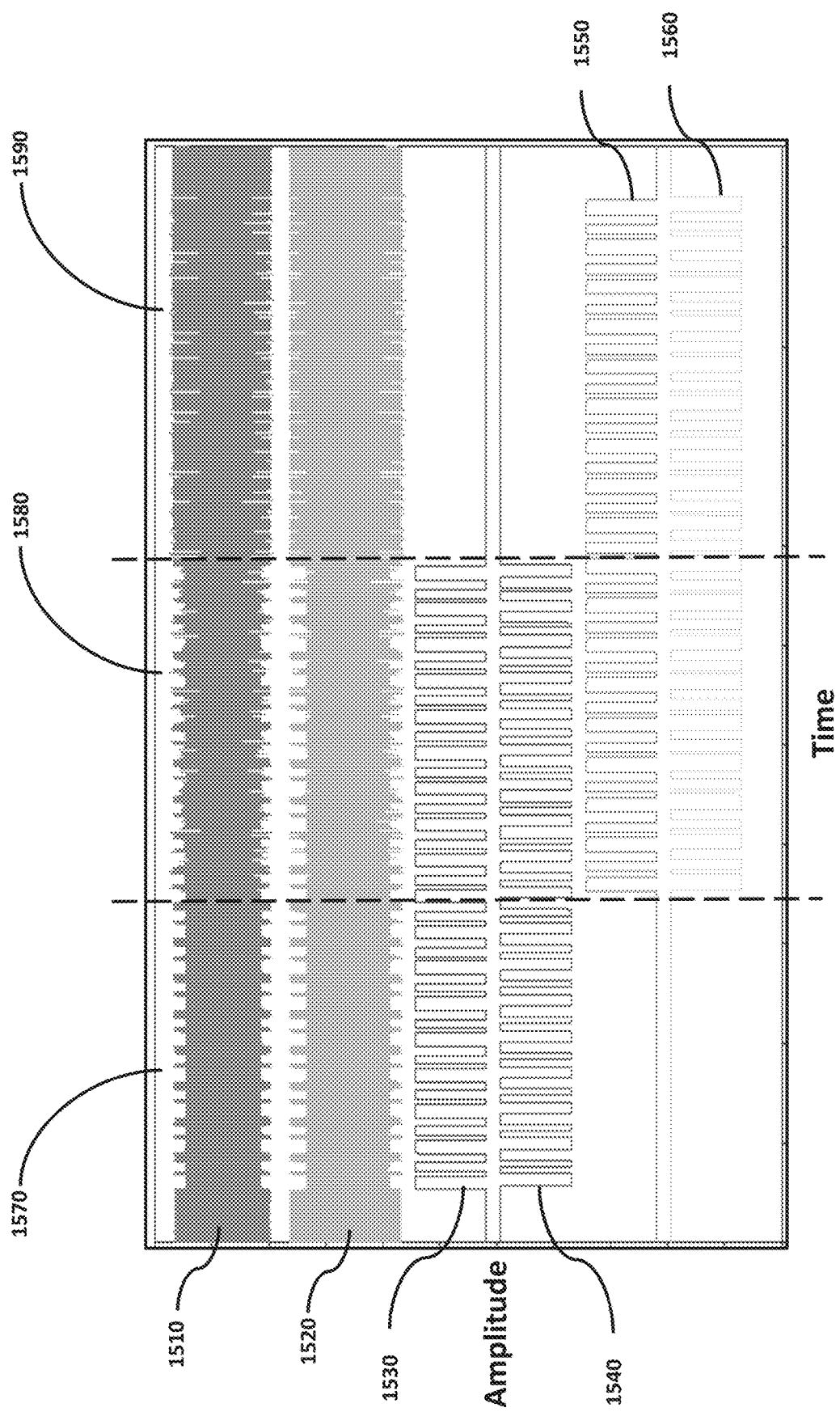
FIG. 15 illustrates the bidirectional transfer of data by using PSK and AM modulation, in accordance with an example embodiment herein.

Because PSK and AM modulation and detection are orthogonal signaling schemes, they may be employed to transfer data bidirectionally and simultaneously. FIG. 15 illustrates the various modes of bidirectional data transfer using PSK and AM modulation, in accordance with an example embodiment herein. In an inherently electrically noisy environment (for instance, such as electrosurgery), AM noise may be undesirably added to PSK demodulation during AM modulation and PSK noise may be undesirably added to AM demodulation during PSK modulation. Such interference and/or cross-talk due to AM and PSK noise may be mitigated and/or avoided by transferring data in each direction in respectively separate time slices (such that, at any given time, only one of AM and PSK data communication is being performed). To illustrate this, FIG. 15 shows three separate modes of communication. In a first mode shown in portion 1570 of the waveforms, only AM modulation and demodulation are being performed (for instance, to communicate second data from the secondary side to the primary side of the isolation circuitry 1010). In a second mode shown in portion 1590 of the waveforms, only PSK modulation and demodulation are being performed (for instance, to communicate first data from the primary side to the secondary side of the isolation circuitry 1010). And in a third mode shown in portion 1580 of the waveforms, both AM modulation and demodulation and PSK modulation and demodulation are being performed simultaneously.

As can be appreciated in view of the present disclosure, an improved system is provided for effective and efficient transfer of power and data in both directions, across an isolation boundary, between an energy source and a surgical instrument. The system provides a reliable and cost-effective power and data interface that may be realized using a relatively small footprint, and that may facilitate repeatable device performance, efficient and stable energy transfer, relatively low parasitic capacitance from patient isolation to ground, and reliable bidirectional transfer of data across the patient isolation boundary using relatively high data rates.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
   a power supply;
   a surgical instrument; and
   a power and data interface assembly, comprising:
      a transformer having a primary winding and a secondary winding;
      a first modulator coupled to the primary winding and configured to receive a power signal from the power supply;
      a first demodulator coupled to the secondary winding;
      a second modulator coupled to the secondary winding;
      a second demodulator coupled to the primary winding; and
      at least one capacitor configured to tune the primary winding to a first resonant frequency and tune the secondary winding to a second resonant frequency different than the first resonant frequency.

2. The surgical system according to claim 1, wherein the transformer is an air core transformer.

3. The surgical system according to claim 1, wherein the first resonant frequency is within a range of 200 kilohertz to 1 gigahertz.

4. The surgical system according to claim 1, wherein the second resonant frequency is within a range of 200 kilohertz to 1 gigahertz.

5. The surgical system according to claim 1, wherein power from the power signal is delivered to the surgical instrument via the transformer.

6. The surgical system according to claim 1,
   wherein the first demodulator is configured to:
      demodulate, according to a first type of modulation, a modulated power signal to obtain first data; and
      communicate the first data to a second processor; and
   wherein the second demodulator is configured to:
      demodulate, according to a second type of modulation, a modulated second signal to obtain second data, and
      communicate the second data to a first processor.

7. The surgical system according to claim 6, wherein the first data is generated by the first processor and includes control information for controlling the surgical instrument, and the second data is generated by the second processor based on a sensor signal received from a sensor.

8. The surgical system according to claim 7, wherein the control information includes at least one of temperature data, device calibration data, device usage data, force data, or orientation data.

9. The surgical system according to claim 7, wherein the sensor includes at least one of a hand switch closure detection sensor configured to detect closure of a hand switch of the surgical instrument or a return electrode monitoring sensor configured to detect an impedance associated with a return electrode.

10. The surgical system according to claim 6, wherein a first type of modulation and a second type of modulation are configured for simultaneous bi-directional communication of the first data and the second data via the transformer.

11. The surgical system according to claim 1, further comprising:
   a first processor configured to communicate first data to a second processor via the first modulator, the transformer, and the first demodulator, the second processor configured to communicate second data to the first processor via the second modulator, the transformer, and the second demodulator.

12. The surgical system according to claim 1, wherein the first modulator is configured to perform a phase shift keying modulation and the second modulator is configured to perform an amplitude modulation.

13. A power and data interface assembly, comprising:
   a transformer having a primary winding and a secondary winding;
   a first modulator coupled to the primary winding and configured to receive a power signal from a power supply;
   a first demodulator coupled to the secondary winding;
   a second modulator coupled to the secondary winding;
   a second demodulator coupled to the primary winding; and
   at least one capacitor configured to tune the primary winding to a first resonant frequency and tune the secondary winding to a second resonant frequency different than the first resonant frequency.

14. The power and data interface assembly according to claim 13, wherein the transformer is an air core transformer.

15. The power and data interface assembly according to claim 13, wherein the first resonant frequency is within a range of 200 kilohertz to 1 gigahertz.

16. The power and data interface assembly according to claim 13, wherein the second resonant frequency is within a range of 200 kilohertz to 1 gigahertz.

17. The power and data interface assembly according to claim 13, wherein power from the power signal is delivered to a surgical instrument via the transformer.

18. The power and data interface assembly according to claim 13,
   wherein the first demodulator is configured to:
      demodulate, according to a first type of modulation, a modulated power signal to obtain first data and
      communicate the first data to a second processor; and
   wherein the second demodulator is configured to:
      demodulate, according to a second type of modulation, a modulated second signal to obtain second data; and
      communicate the second data to a first processor.

19. The power and data interface assembly according to claim 18, wherein the first data is generated by the first processor and includes control information for controlling a surgical instrument, and the second data is generated by the second processor based on a sensor signal received from a sensor, the control information including at least one of temperature data, device calibration data, device usage data, force data, or orientation data.

20. The power and data interface assembly according to claim 19, wherein the sensor includes at least one of a hand switch closure detection sensor configured to detect closure of a hand switch of a surgical instrument or a return electrode monitoring sensor configured to detect an impedance associated with a return electrode.

* * * * *